United States Patent
Lazzari et al.

(10) Patent No.: US 7,002,010 B2
(45) Date of Patent: Feb. 21, 2006

(54) PROCESS FOR THE PREPARATION OF MORPHOLINONES AS LIGHT STABILIZERS

(75) Inventors: Dario Lazzari, Bologna (IT); Mirko Rossi, San Lazzaro di Savena (IT); Giuseppe Veronesi, Bologna (IT); Nazzareno Ruggeri, San Benedetto Val di Sambro (IT); Katharina Fritzsche, Weil am Rhein (DE); Adalbert Braig, Binzen (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 337 days.

(21) Appl. No.: 10/432,265

(22) PCT Filed: Dec. 4, 2001

(86) PCT No.: PCT/EP01/14179

§ 371 (c)(1),
(2), (4) Date: May 21, 2003

(87) PCT Pub. No.: WO02/48123

PCT Pub. Date: Jun. 20, 2002

(65) Prior Publication Data

US 2004/0024252 A1 Feb. 5, 2004

(30) Foreign Application Priority Data

Dec. 12, 2000 (EP) ............................................. 00811175

(51) Int. Cl.
*C07C 229/06* (2006.01)
*C07C 217/04* (2006.01)
*C07D 265/32* (2006.01)

(52) U.S. Cl. ...................... 544/172; 562/518; 562/567; 564/508; 502/522; 502/523

(58) Field of Classification Search ................. 544/172; 562/518, 567; 564/508; 502/522, 523
See application file for complete search history.

(56) References Cited

FOREIGN PATENT DOCUMENTS

WO 99/14206 3/1999

*Primary Examiner*—Brian Davis
(74) *Attorney, Agent, or Firm*—Joseph Suhadolnik

(57) ABSTRACT

The instant invention discloses a process for the preparation of compounds of the formula I:

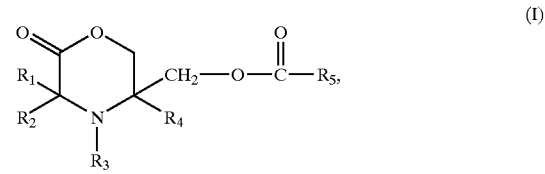

wherein the general symbols are as defined in claim 1, which process comprises reacting a compound of formula II:

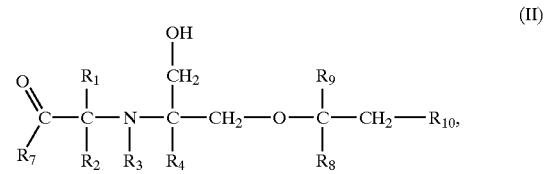

wherein the general symbols are as defined in claim 1, with a compound of the formula III:

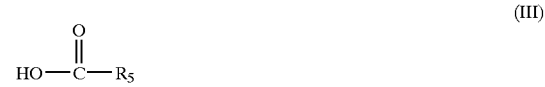

wherein $R_5$ is as defined in claim 1. The compounds of the formula II are new and useful as stabilizers for protecting organic materials, in particular synthetic polymers, reprographic materials or coating materials against oxidative, thermal or light-induced degradation.

21 Claims, No Drawings

PROCESS FOR THE PREPARATION OF MORPHOLINONES AS LIGHT STABILIZERS

This application is a 371 of PCT/EP01/14179 filed Dec. 4, 2000.

The present invention relates to a novel process for the preparation of morpholinones starting from new intermediates which are also suitable for stabilizing organic materials against oxidative, thermal or light-induced degradation.

The best process hitherto for the preparation of morpholinones is described, for example, in WO-A-99/14206. Example A1 in this reference discloses the use of 2-amino-2-methyl-1,3-propanediol [AMPD] as a starting material. This starting material has several disadvantages which are, for example, low solubility of AMPD in lipophilic solvents, difficulties in recycling the excess of AMPD, yields of usually lower than 60% of morpholinones and difficulties in controlling the exothermic reaction of AMPD with chloroform and base.

There is therefore still a need to find an efficient process for the preparation of morpholinones that does not have the disadvantages mentioned above.

The present invention therefore relates to a process for the preparation of compounds of the formula I:

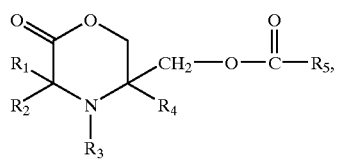

(I)

wherein $R_1$ and $R_2$ are each independently of the other $C_1$–$C_{18}$alkyl, $C_2$–$C_{18}$alkyl which is interrupted by oxygen or by

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy; or $R_1$ and $R_2$, together with the carbon atom to which they are bonded, form a $C_5$–$C_8$cycloalkylidene ring unsubstituted or substituted by from 1 to 3 $C_1$–$C_4$alkyl groups;

$R_3$ is hydrogen, $C_1$–$C_{18}$alkyl, $C_2$–$C_{18}$alkyl which is interrupted by oxygen or by

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy; $C_1$–$C_{12}$alkoxy, $C_5$–$C_{12}$cycloalkoxy, $C_2$–$C_{12}$alkenyloxy, $C_7$–$C_2$phenylalkoxy, $C_7$–$C_{12}$phenylalkoxy substituted by hydroxy, $C_1$–$C_4$alkyl and/or $C_1$–$C_4$alkoxy;

$R_4$ is $C_1$–$C_{18}$alkyl, $C_2$–$C_{18}$alkyl which is interrupted by oxygen or by

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy;

$R_5$ is $C_1$–$C_{18}$alkyl, $C_2$–$C_{18}$alkyl which is interrupted by oxygen; $C_1$–$C_{18}$alkyl which is substituted by hydroxy;

$R_6$ is hydrogen, $C_1$–$C_{18}$alkyl, $C_2$–$C_{18}$alkyl which is interrupted by oxygen; $C_2$–$C_{18}$alkyl which is substituted by hydroxy; or $C_7$–$C_{12}$phenylalkyl, which process comprises reacting a compound of the formula II:

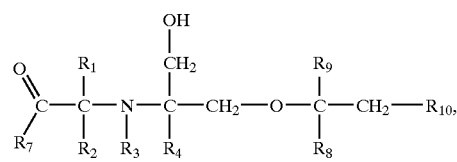

(II)

wherein $R_1$, $R_2$, $R_3$ and $R_4$ are as defined above, $R_7$ is hydroxy,

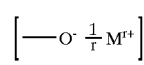

or $C_1$–$C_{18}$alkoxy, $R_8$ and $R_9$ are each independently of the other $C_1$–$C_{18}$alkyl, $C_2$–$C_{18}$alkyl which is interrupted by oxygen or by

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy;

$R_{10}$ is hydrogen, $C_1$–$C_{18}$alkyl, $C_2$–$C_{18}$alkyl which is interrupted by oxygen or by

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy;

M is a r-valent metal cation, and r is 1, 2 or 3, with a compound of the formula III:

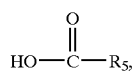  (III)

wherein $R_5$ is as defined above.

Alkyl having up to 18 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetra-methylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl or octadecyl.

$C_2$–$C_{18}$Alkyl interrupted by oxygen or by

is, for example, $CH_3$—O—$CH_2$—, $CH_3$—N($CH_3$)—$CH_2$—, $CH_3$—O—$CH_2CH_2$—O—$CH_2CH_2$—, $CH_3$—(O—$CH_2CH_2$—)$_2$O—$CH_2CH_2$—, $CH_3$—(O—$CH_2CH_2$—)$_3$O—$CH_2CH_2$— or $CH_3$—(O—$CH_2CH_2$—)$_4$O—$CH_2CH_2$—.

$C_1$–$C_{18}$Alkyl which is substituted by hydroxy is a branched or unbranched radical which contains preferably 1 to 3, in particular 1 or 2, hydroxyl groups, such as, for example, hydroxyethyl, 3-hydroxypropyl, 2-hydroxypropyl, 4-hydroxybutyl, 3-hydroxybutyl, 2-hydroxybutyl, 5-hydroxypentyl, 4-hydroxypentyl, 3-hydroxypentyl, 2-hydroxypentyl, 6-hydroxyhexyl, 5-hydroxyhexyl, 4-hydroxyhexyl, 3-hydroxyhexyl, 2-hydroxyhexyl, 7-hydroxyheptyl, 6-hydroxyheptyl, 5-hydroxyheptyl, 4-hydroxyheptyl, 3-hydroxyheptyl, 2-hydroxyheptyl, 8-hydroxyoctyl, 7-hydroxyoctyl, 6-hydroxyoctyl, 5-hydroxyoctyl, 4-hydroxyoctyl, 3-hydroxyoctyl, 2-hydroxyoctyl, 9-hydroxynonyl, 10-hydroxydecyl, 11-hydroxyundecyl, 12-hydroxydodecyl, 13-hydroxytridecyl, 14-hydroxytetradecyl, 15-hydroxypentadecyl, 16-hydroxyhexadecyl, 17-hydroxyheptadecyl or 18-hydroxyoctadecyl.

$C_7$–$C_{12}$Phenylalkyl is, for example, benzyl, α-methylbenzyl, α,α-dimethylbenzyl, 2-phenylethyl, 3-phenylpropyl, 4-phenylbutyl, 5-phenylpentyl or 6-phenylhexyl. Preference is given to benzyl and α,α-dimethylbenzyl.

$C_7$–$C_{12}$phenylalkyl substituted by hydroxy, $C_1$–$C_4$alkyl and/or $C_1$–$C_4$alkoxy is a branched or unbranched radical which contains preferably 1 to 3, in particular 1 or 2, hydroxy, $C_1$–$C_4$alkyl or $C_1$–$C_4$alkoxy groups, such as, for example, 4-hydroxybenzyl, 4-methylbenzyl, 4-methoxybenzyl, 4-methyl-α,α-dimethylbenzyl, 2,4,6-trimethylbenzyl, 2,4,6-trimethyl-α,α-dimethylbenzyl, 4-methoxy-α,α-dimethylbenzyl, 4-tert-butyl-benzyl or 4-(4-tert-butylphenyl)butyl.

Unsubstituted $C_5$–$C_{12}$cycloalkyl or $C_5$–$C_{12}$cycloalkyl substituted by hydroxy, $C_1$–$C_4$alkyl and/or $C_1$–$C_4$alkoxy is, for example, cyclopentyl, methylcyclopentyl, dimethylcyclopentyl, cyclohexyl, 4-hydroxycyclohexyl, 4-methoxycyclohexyl, methylcyclohexyl, dimethylcyclohexyl, trimethylcyclohexyl, tert-butylcyclohexyl, cycloheptyl or cyclooctyl. Preference is given to cyclohexyl and tert-butylcyclohexyl.

A $C_5$–$C_8$cycloalkylidene ring substituted by $C_1$–$C_4$alkyl, which contains preferably from 1 to 3, especially 1 or 2, branched or unbranched alkyl group radicals, is, for example, cyclopentylidene, methylcyclopentylidene, dimethylcyclopentylidene, cyclohexylidene, methylcyclohexylidene, dimethylcyclohexylidene, trimethylcyclohexylidene, tert-butylcyclohexylidene, cycloheptylidene or cyclooctylidene. Preference is given to cyclohexylidene and tert-butylcyclohexylidene.

Alkoxy having up to 18 carbon atoms is a branched or unbranched radical, for example methoxy, ethoxy, propoxy, isopropoxy, n-butoxy, isobutoxy, pentyloxy, isopentyloxy, hexyloxy, heptyloxy, octyloxy, decyloxy, undecyloxy, dodecyloxy, hexadecyloxy or octadecyloxy.

$C_5$–$C_{12}$cycloalkoxy is, for example, cyclopentyloxy, cyclohexyloxy, cycloheptyloxy, cyclooctyloxy, cyclononyloxy, cyclodecyloxy, cycloundecyloxy or cyclododecyloxy. Preference is given to cyclohexyloxy.

Alkenyloxy of 2 to 12 carbon atoms is a branched or unbranched radical, for example vinyloxy, propenyloxy, 2-butenyloxy, 3-butenyloxy, isobutenyloxy, n-2,4-pentadienyloxy, 3-methyl-2-butenyloxy, n-2-octenyloxy, n-2-dodecenyloxy, isododecenyloxy, oleyloxy, n-2-octadecenyloxy or n-4-octadecenyloxy. It is preferred to use alkenyloxy of 3 to 12, in particular of 3 to 6, most preferably of 3 to 4, carbon atoms.

Unsubstituted $C_7$–$C_{12}$phenylalkoxy or $C_7$–$C_{12}$phenylalkoxy substituted by hydroxy, $C_1$–$C_4$alkyl and/or $C_1$–$C_4$alkoxy is a branched or unbranched radical which contains preferably 1 to 3, in particular 1 or 2, hydroxy, $C_1$–$C_4$alkyl or $C_1$–$C_4$alkoxy groups, such as, for example, benzyloxy, 4-hydroxybenzyloxy, 4-methylbenzyloxy, 4-methoxybenzyloxy, α-methylbenzyloxy, α,α-dimethylbenzyloxy, 4-methyl-α,α-dimethylbenzyloxy, 2,4,6-trimethylbenzyloxy, 2,4,6-trimethyl-α,α-dimethylbenzyloxy, 4-methoxy-α,α-dimethylbenzyloxy, 4-tert-butyl-benzyloxy or 4-(4-tert-butylphenyl)butoxy.

A mono-, di- or tri-valent metal cation is preferably an alkali metal cation, alkaline earth metal cation or aluminium cation, for example $Na^+$, $K^+$, $Mg^{++}$, $Ca^{++}$ or $Al^{+++}$.

Of interest is a process for the preparation of compounds of formula I wherein $R_1$ and $R_2$ are each independently of the other $C_1$–$C_{12}$alkyl, $C_2$–$C_{12}$alkyl which is interrupted by oxygen or by

$C_1$–$C_{12}$alkyl which is substituted by hydroxy; $C_7$–$C_9$phenylalkyl, $C_7$–$C_9$phenylalkyl substituted by $C_1$–$C_4$alkyl and/or $C_1$–$C_4$alkoxy; $C_5$–$C_8$cycloalkyl, $C_5$–$C_8$cycloalkyl substituted by $C_1$–$C_4$alkyl and/or $C_1$–$C_4$alkoxy; or $R_1$ and $R_2$, together with the carbon atom to which they are bonded, form a $C_5$–$C_8$cycloalkylidene;

$R_3$ is hydrogen, $C_1$–$C_{12}$alkyl, $C_2$–$C_{12}$alkyl which is interrupted by oxygen or by

$C_1$–$C_{12}$alkyl which is substituted by hydroxy; $C_7$–$C_9$phenylalkyl, $C_7$–$C_9$phenylalkyl substituted by $C_1$–$C_4$alkyl and/or $C_1$–$C_4$alkoxy; $C_5$–$C_8$cycloalkyl, $C_5$–$C_8$cycloalkyl substituted by $C_1$–$C_4$alkyl and/or $C_1$–$C_4$alkoxy; $C_1$–$C_8$alkoxy, $C_5$–$C_8$cycloalkoxy, $C_2$–$C_8$alkenyloxy, $C_7$–$C_9$phenylalkoxy, $C_7$–$C_9$phenylalkoxy substituted by $C_1$–$C_4$alkyl and/or $C_1$–$C_4$alkoxy;

$R_4$ is $C_1$–$C_{12}$alkyl, $C_2$–$C_{12}$alkyl which is interrupted by oxygen or by

$C_1$–$C_{12}$alkyl which is substituted by hydroxy; $C_7$–$C_9$phenylalkyl, $C_7$–$C_9$phenylalkyl substituted $C_1$–$C_4$alkyl and/or $C_1$–$C_4$alkoxy; $C_5$–$C_8$cycloalkyl, $C_5$–$C_8$cycloalkyl substituted by $C_1$–$C_4$alkyl and/or $C_1$–$C_4$alkoxy;

$R_5$ is $C_1$–$C_{12}$alkyl, $C_2$–$C_{12}$alkyl which is interrupted by oxygen; $C_1$–$C_{12}$alkyl which is substituted by hydroxy;

$R_6$ is hydrogen, $C_1$–$C_{12}$alkyl, $C_2$–$C_{12}$alkyl which is interrupted by oxygen; $C_2$–$C_{12}$alkyl which is substituted by hydroxy; or $C_7$–$C_{12}$phenylalkyl, $R_7$ is hydroxy,

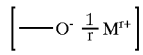

or $C_1$–$C_{12}$alkoxy, $R_8$ and $R_9$ are each independently of the other $C_1$–$C_{12}$alkyl, $C_2$–$C_{12}$alkyl which is interrupted by oxygen or by

$C_1$–$C_{12}$alkyl which is substituted by hydroxy; $C_7$–$C_9$phenylalkyl, $C_7$–$C_9$phenylalkyl substituted by $C_1$–$C_4$alkyl and/or $C_1$–$C_4$alkoxy; $C_5$–$C_8$cycloalkyl, $C_5$–$C_8$cycloalkyl substituted by $C_1$–$C_4$alkyl and/or $C_1$–$C_4$alkoxy;

$R_{10}$ is hydrogen, $C_1$–$C_{12}$alkyl, $C_2$–$C_{12}$alkyl which is interrupted by oxygen or by

$C_1$–$C_{12}$alkyl which is substituted by hydroxy; $C_7$–$C_9$phenylalkyl, $C_7$–$C_9$phenylalkyl substituted by $C_1$–$C_4$alkyl and/or $C_1$–$C_4$alkoxy; $C_5$–$C_8$cycloalkyl, $C_5$–$C_8$cycloalkyl substituted by $C_1$–$C_4$alkyl and/or $C_1$–$C_4$alkoxy;

M is a r-valent metal cation, and
r is 1 or 2.

Likewise of interest is a process for the preparation of compounds of formula I wherein $R_1$ and $R_2$ are each independently of the other $C_1$–$C_8$alkyl, $C_2$–$C_8$alkyl which is interrupted by oxygen; $C_1$–$C_8$alkyl which is substituted by hydroxy; benzyl, cyclohexyl; or $R_1$ and $R_2$, together with the carbon atom to which they are bonded, form a cyclohexylidene;

$R_3$ is hydrogen, $C_1$–$C_8$alkyl, $C_2$–$C_8$alkyl which is interrupted by oxygen; $C_1$–$C_8$alkyl which is substituted by hydroxy; benzyl, cyclohexyl, $C_1$–$C_8$alkoxy, cyclohexyloxy or benzyloxy;

$R_4$ is $C_1$–$C_8$alkyl, $C_2$–$C_8$alkyl which is interrupted by oxygen; $C_1$–$C_8$alkyl which is substituted by hydroxy; benzyl or cyclohexyl, $R_5$ is $C_1$–$C_{12}$alkyl or $C_1$–$C_{12}$alkyl which is substituted by hydroxy;

$R_7$ is hydroxy,

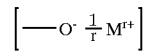

or $C_1$–$C_4$alkoxy, $R_8$ and $R_9$ are each independently of the other $C_1$–$C_8$alkyl, $C_2$–$C_8$alkyl which is interrupted by oxygen; $C_1$–$C_8$alkyl which is substituted by hydroxy; benzyl or cyclohexyl, $R_{10}$ is hydrogen, $C_1$–$C_8$alkyl, $C_2$–$C_8$alkyl which is interrupted by oxygen; $C_1$–$C_8$alkyl which is substituted by hydroxy; benzyl or cyclohexyl, M is sodium, potassium, magnesium or calcium, and
r is 1 or 2.

Of special interest is a process for the preparation of compounds of formula I wherein
$R_1$ and $R_2$ are $C_1$–$C_4$alkyl,
$R_3$ is hydrogen or methyl,
$R_4$ is $C_1$–$C_4$alkyl,
$R_5$ is $C_1$–$C_{10}$alkyl,
$R_7$ is hydroxy or

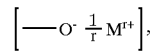

$R_8$ is $C_1$–$C_4$alkyl,
$R_9$ is $C_1$–$C_4$alkyl,
$R_{10}$ is hydrogen or $C_1$–$C_4$alkyl,
M is lithium, sodium, potassium or calcium, and
r is 1 or 2.

Likewise of special interest is a process for the preparation of compounds of formula I wherein
$R_1$ and $R_2$ are methyl,
$R_3$ is hydrogen,
$R_4$ is methyl or ethyl,
$R_5$ is $C_6$–$C_8$alkyl,
$R_7$ is

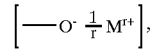

$R_8$ is methyl,
$R_9$ is methyl,
$R_{10}$ is hydrogen,
M is sodium, and
r is 1.

Special preference is given to a process for the preparation of compounds of formula I which process comprises reacting a compound of the formula II with a compound of the formula III in the presence of a catalyst. The amount of catalyst is preferably used in 0.01 to 5%, e.g. 0.1 to 1%, based on the weight of the compound of the formula II. Catalysts of special interest are Brönstedt acids or Lewis acids.

Brönstedt acids are for example hydrochloric acid, hydrobromic acid, hypophosphorous acid, phosphoric acid or sulfuric acid.

Lewis acids are for example tin(II)oxide or tin(II) carboxylates.

Preferred reaction conditions for the process according to the invention are as follows:

The reaction may be carried out at an elevated temperature, especially at temperatures of from 20 to 200° C., preferably of from 80 to 190° C., e.g. from 150 to 180° C., in a solvent.

Preferred solvents are for example lipophilic solvents like for example petroleum in a boiling range of 160–180° C.

The compound of the formula III is preferably used in at least an equal molar amount in respect to the compound of the formula II. Preferably, the molar ratio between the compound of the formula III and the compound of the formula II is 4:1 to 1:1; especially 2:1 to 1:1, for example 1.3:1 to 1:1;

The starting compounds of formula II are new. The present invention therefore relates also to new compounds of the formula II

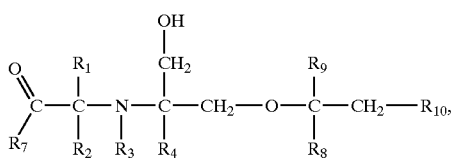

(II)

wherein $R_1$ and $R_2$ are each independently of the other $C_1$–$C_{18}$alkyl, $C_2$–$C_{18}$alkyl which is interrupted by oxygen or by

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy; or $R_1$ and $R_2$, together with the carbon atom to which they are bonded, form a $C_5$–$C_8$cycloalkylidene ring unsubstituted or substituted by from 1 to 3 $C_1$–$C_4$alkyl groups;

$R_3$ is hydrogen, $C_1$–$C_{18}$alkyl, $C_2$–$C_{18}$alkyl which is interrupted by oxygen or by

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy; $C_1$–$C_{12}$alkoxy, $C_5$–$C_{12}$cycloalkoxy, $C_2$–$C_{12}$alkenyloxy, $C_7$–$C_{12}$phenylalkoxy, $C_7$–$C_{12}$phenylalkoxy substituted by hydroxy, $C_1$–$C_4$alkyl and/or $C_1$–$C_4$alkoxy;

$R_4$ is $C_1$–$C_{18}$alkyl, $C_2$–$C_{18}$alkyl which is interrupted by oxygen or by

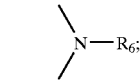

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy;

$R_6$ is hydrogen, $C_1$–$C_{18}$alkyl, $C_2$–$C_{18}$alkyl which is interrupted by oxygen; $C_2$–$C_{18}$alkyl which is substituted by hydroxy; or $C_7$–$C_{12}$phenylalkyl, $R_7$ is hydroxy,

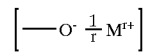

or $C_1$–$C_{18}$alkoxy, $R_8$ and $R_9$ are each independently of the other $C_1$–$C_{18}$alkyl, $C_2$–$C_{18}$alkyl which is interrupted by oxygen or by

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy;

$R_{10}$ is hydrogen, $C_1$–$C_{18}$alkyl, $C_2$–$C_{18}$alkyl which is interrupted by oxygen or by

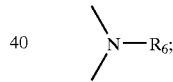

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy;

M is a r-valent metal cation, and r is 1, 2 or 3.

The definitions of the general symbols for the new compounds of the formula II according to the invention are the same as for the process for the preparation of the compounds of the formula I discussed hereinbefore.

Of very special interest are compounds of the formula II wherein $R_1$ and $R_2$ are $C_1$–$C_4$alkyl, $R_3$ is hydrogen or methyl, $R_4$ is $C_1$–$C_4$alkyl, $R_7$ is hydroxy or

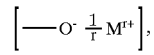

$R_8$ is $C_1$–$C_4$alkyl, $R_9$ is $C_1$–$C_4$alkyl, $R_{10}$ is hydrogen or $C_1$–$C_4$alkyl, M is lithium, sodium, potassium or calcium, and r is 1 or 2.

The invention relates also to a novel process for the preparation of compounds of the formula II

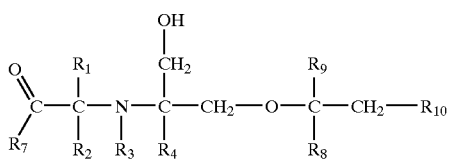
(II)

wherein $R_1$ and $R_2$ are each independently of the other $C_1$–$C_{18}$alkyl, $C_2$–$C_{18}$alkyl which is interrupted by oxygen or by

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy; or $R_1$ and $R_2$, together with the carbon atom to which they are bonded, form a $C_5$–$C_8$cycloalkylidene ring unsubstituted or substituted by from 1 to 3 $C_1$–$C_4$alkyl groups;

$R_3$ is hydrogen, $C_1$–$C_{18}$alkyl, $C_2$–$C_{18}$alkyl which is interrupted by oxygen or by

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy; $C_1$–$C_{12}$alkoxy, $C_5$–$C_{12}$cycloalkoxy, $C_2$–$C_{12}$alkenyloxy, $C_7$–$C_{12}$phenylalkoxy, $C_7$–$C_{12}$phenylalkoxy substituted by hydroxy, $C_1$–$C_4$alkyl and/or $C_1$–$C_4$alkoxy;

$R_4$ is $C_1$–$C_{18}$alkyl, $C_2$–$C_{18}$alkyl which is interrupted by oxygen or by

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy;

$R_6$ is hydrogen, $C_1$–$C_{18}$alkyl, $C_2$–$C_{18}$alkyl which is interrupted by oxygen; $C_2$–$C_{18}$alkyl which substituted by hydroxy; or $C_7$–$C_{12}$phenylalkyl, $R_7$ is hydroxy,

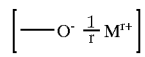

or $C_1$–$C_{18}$alkoxy, $R_8$ and $R_9$ are each independently of the other $C_1$–$C_{18}$alkyl, $C_2$–$C_{18}$alkyl which is interrupted by oxygen or by

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy;

$R_{10}$ is hydrogen, $C_1$–$C_{18}$alkyl, $C_2$–$C_{18}$alkyl which is interrupted by oxygen or by

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy;

M is a r-valent metal cation, and r is 1, 2 or 3;

which process comprises reacting a compound of the formula IV:

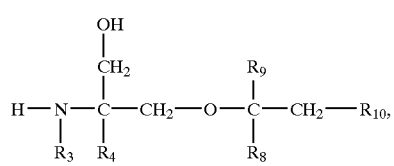
(IV)

wherein $R_3$, $R_4$, $R_8$, $R_9$ and $R_{10}$ are as defined above, with a compound of the formula V:

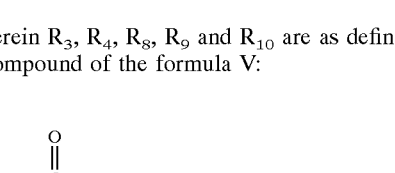
(V)

wherein $R_1$ and $R_2$ are as defined above, and chloroform in the presence of a base.

Preferred reaction conditions for this process are as follows:

The reaction may be carried out at an elevated temperature, especially at temperatures of from 10 to 100° C., preferably of from 10 to 60° C., e.g. from 20 to 30° C.

Preferred bases are for example metal hydroxides as for example sodium hydroxide, potassium hydroxide or calcium hydroxide.

The compound of the formula V is preferably used in at least an equal molar amount in respect to the compound of the formula IV. Preferably, the compound of the formula V is also used as a solvent. Of interest is therefore a molar ratio between the compound of the formula V and the compound of the formula IV of 200:1 to 1:1; especially 100:1 to 1:1, for example 90:1 to 1:1.

The starting compounds of formula IV are also new. The present invention therefore relates also to new compounds of the formula IV:

$$
\begin{array}{c}
\text{OH} \\
| \\
\text{CH}_2 \quad\quad R_9 \\
| \quad\quad\quad | \\
\text{H}-\text{N}-\text{C}-\text{CH}_2-\text{O}-\text{C}-\text{CH}_2-R_{10}, \\
| \quad | \quad\quad\quad | \\
R_3 \; R_4 \quad\quad\quad R_8
\end{array}
\tag{IV}
$$

wherein $R_3$ is hydrogen, $C_1$–$C_{18}$alkyl, $C_2$–$C_{18}$alkyl which is interrupted by oxygen or by $$\diagdown\!\!\!\!{\rm N}\!-\!R_6;\diagup$$

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy; $C_1$–$C_{12}$alkoxy, $C_5$–$C_{12}$cycloalkoxy, $C_2$–$C_{12}$alkenyloxy, $C_7$–$C_{12}$phenylalkoxy, $C_7$–$C_{12}$phenylalkoxy substituted by hydroxy, $C_1$–$C_4$alkyl and/or $C_1$–$C_4$alkoxy;

$R_4$ is $C_1$–$C_{18}$alkyl, $C_2$–$C_{18}$alkyl which is interrupted by oxygen or by $$\diagdown\!\!\!\!{\rm N}\!-\!R_6;\diagup$$

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy;

$R_6$ is hydrogen, $C_1$–$C_{18}$alkyl, $C_2$–$C_{18}$alkyl which is interrupted by oxygen; $C_2$–$C_{18}$alkyl which is substituted by hydroxy; or $C_7$–$C_{12}$phenylalkyl, $R_8$ and $R_9$ are each independently of the other $C_1$–$C_{18}$alkyl, $C_2$–$C_{18}$alkyl which is interrupted by oxygen or by $$\diagdown\!\!\!\!{\rm N}\!-\!R_6;\diagup$$

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy;

$R_{10}$ is hydrogen, $C_1$–$C_{18}$alkyl, $C_2$–$C_{18}$alkyl which is interrupted by oxygen or by $$\diagdown\!\!\!\!{\rm N}\!-\!R_6;\diagup$$

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy.

The definitions of the general symbols for the new compounds of the formula IV according to the invention are the same as for the process for the preparation of the compounds of the formula I discussed hereinbefore.

Of very special interest are compounds of the formula IV wherein
  $R_3$ is hydrogen or methyl,
  $R_4$ is $C_1$–$C_4$alkyl,
  $R_8$ and $R_9$ is $C_1$–$C_4$alkyl, and
  $R_{10}$ is hydrogen or $C_1$–$C_4$alkyl.

A preferred process for the preparation of the compounds of the formula IV starts from a compound of the formula VI:

$$R_4-CH_2-NO_2 \tag{VI}$$

wherein $R_4$ is as defined above.

The instant invention relates also to a multi-step process for the preparation of compounds of the formula I:

$$
\begin{array}{c}
\text{O}\!\!=\!\!\overset{\displaystyle\diagup\!\!\!\!\!\text{O}}{\underset{R_2}{\underset{|}{\overset{R_1}{\overset{|}{C}}}}}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!
\end{array}
\tag{I}
$$

(ring: O=C–O–CH(R_1,R_2)–N(R_3)–C(R_4)(CH_2–O–C(=O)–R_5)– )

wherein the general symbols are as defined above, which comprises in successive steps a) reacting a compound of the formula VI:

$$R_4-CH_2-NO_2 \tag{VI},$$

wherein $R_4$ is as defined above, with formaldehyde in the presence of a base to give the compound of the formula VII:

$$O_2N-\underset{\underset{R_4}{|}}{CH}-CH_2-OH, \tag{VII}$$

and then b) reacting this compound of the formula VII with a compound of the formula VIII or IX:

$$\underset{R_4}{\overset{R_9}{\diagdown}}\!\!C\!\!=\!\!CH-R_{10} \tag{VIII}$$

$$HO-\underset{\underset{R_8}{|}}{\overset{\overset{R_9}{|}}{C}}-CH_2-R_{10} \tag{IX}$$

wherein $R_8$, $R_9$ and $R_{10}$ are as defined above, in the presence of a catalyst to give the compound of the formula X:

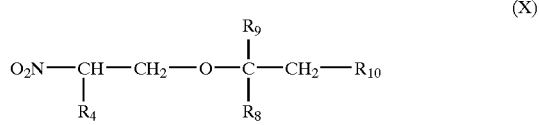
(X)

and then c) reacting this compound of the formula X with formaldehyde in the presence of a base to give the compound of the formula XI:

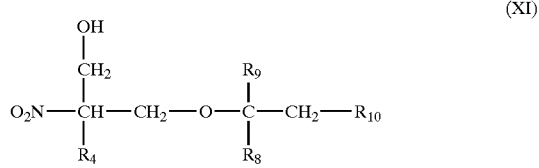
(XI)

and then d) reacting this compound of the formula XI with hydrogen in the presence of a catalyst to give the compound of the formula IV:

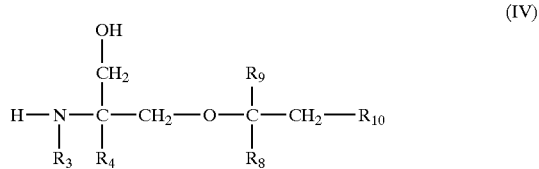
(IV)

wherein $R_3$ is hydrogen, and then e) for obtaining the compounds of the formula IV wherein $R_3$ is different from hydrogen, reacting the compound of the formula IV with an alkylation reagent; and then f) reacting the compound of the formula IV with a compound of the formula V:

(V)

wherein $R_1$ and $R_2$ are as defined in claim 1, and chloroform in the presence of a base to give the compound of the formula II:

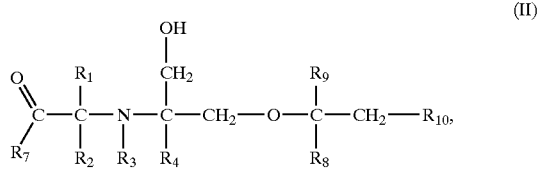
(II)

wherein $R_7$ is as defined above, and then g) for obtaining a compound of the formula II wherein $R_3$ is different from hydrogen, reacting the compound of the formula II, wherein $R_3$ is hydrogen, with an alkylation reagent in case of step e) being not present; and then h) reacting this compound of the formula II with a compound of the formula III:

(III)

wherein $R_5$ is as defined in claim 1; and then i) for obtaining a compound of the formula I wherein $R_3$ is different from hydrogen, reacting the compound of the formula I, wherein $R_3$ is hydrogen, with an alkylation reagent in case of steps e) and g) being not present.

Preferred reaction conditions for this process are as follows:

The reaction of step a) may be carried out at an elevated temperature, especially at temperatures of from 10 to 100° C., preferably of from 30 to 80° C., e.g. from 50 to 80° C.

Preferred bases of step a) are for example metal hydroxides like for example sodium hydroxide, potassium hydroxide or calcium hydroxide.

The formaldehyde in step a) is preferably used in at least an equal molar amount in respect to the compound of the formula VI. Preferably, the compound of the formula VI is also used as a solvent. Of interest is therefore a molar ratio between the compound of the formula VI and formaldehyde of 30:1 to 1:1; especially 20:1 to 1:1, for example 15:1 to 1:1.

The reaction of step b) may be carried out at an elevated temperature, especially at temperatures of from 30 to 100° C., preferably of from 40 to 90° C., e.g. from 50 to 70° C. Preferably, the reaction of step b) may be carried out in a solvent like for example toluene in an autoclave under pressure.

Preferred catalysts of step b) are for example acids like for example p-toluenesulfonic acid or sodium bisulfate [$NaHSO_4$].

The compounds of the formula VII or IX in step b) are preferably used in at least an equal molar amount in respect to the compound of the formula VII. Preferably, the compounds of the formula VII or IX are also used as a solvent. Of interest is therefore a molar ratio between the compounds of the formula VII or IX and the compound of the formula VII of 5:1 to 1:1; especially 4:1 to 1:1, for example 3:1 to 1:1.

The reaction of step c) may be carried out at an elevated temperature, especially at temperatures of from 10 to 100° C., preferably of from 30 to 80° C., e.g. from 50 to 80° C.

Preferred bases of step c) are for example metal hydroxides like for example sodium hydroxide, potassium hydroxide or calcium hydroxide. Preferably, the reaction of step c) may be carried out in a solvent like for example toluene.

The formaldehyde in step c) is preferably used in at least an equal molar amount in respect to the compound of the formula X. Of interest is therefore a molar ratio between the compound of the formula X and formaldehyde of 2:1 to 1:1; especially 1.5:1 to 1:1, for example 1.2:1 to 1:1. Preferably, in reaction step c) a solvent like for example toluene is used.

The reaction of step d) may be carried out at an elevated temperature, especially at temperatures of from 10 to 60° C., preferably of from 20 to 60° C., e.g. from 30 to 50° C. Preferably, the reaction of step d) may be carried out in a solvent like for example toluene in an autoclave under pressure.

Preferred catalysts of step d) are for example hydrogenation catalysts like for Raney-Ni, palladium on charcoal or platinum. The amount of catalyst is preferably used in 0.01 to 5%, e.g. 0.1 to 1%, based on the weight of the compound of the formula XI.

Preferred alkylation reagents for steps e), g) and I) are for example alkyl iodides, alkyl bromides, dialkyl sulfates like for example dimethyl sulfate.

The preferred reaction conditions for steps f) and h) are already outlined above.

The preparation of the compounds of the formula I is also possible via the compounds of the formula XII:

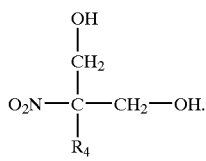
(XII)

The instant invention relates therefore also to a multi-step process for the preparation of compounds of the formula I:

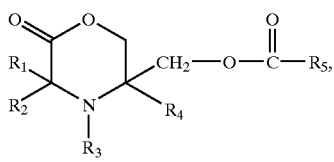
(I)

wherein the general symbols are as defined above, which comprises in successive steps
a) reacting a compound of the formula VI:

(VI), wherein $R_4$ is as defined above, with formaldehyde in the presence of a base to give the compound of the formula XII:

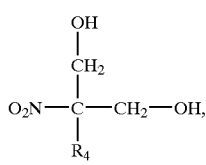
(XII)

and then
b) reacting this compound of the formula XII with a compound of the formula VIII or IX:

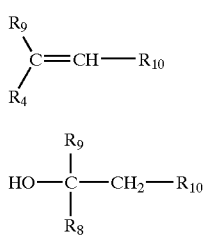
(VIII)

(IX)

wherein $R_8$, $R_9$ and $R_{10}$ are as defined in claim 1, in the presence of a catalyst to give the compound of the formula XI:

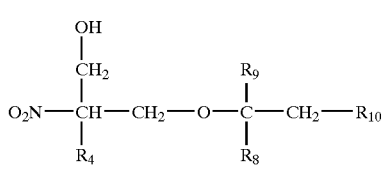
(XI)

and then
c) reacting this compound of the formula XI with hydrogen in the presence of a catalyst to give the compound of the formula IV:

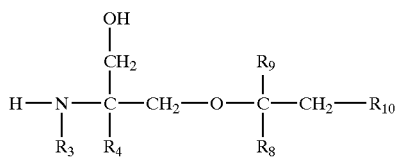
(IV)

wherein $R_3$ is hydrogen, and then
d) for obtaining the compounds of the formula IV wherein $R_3$ is different from hydrogen, reacting the compound of the formula IV with an alkylation reagent; and then
e) reacting the compound of the formula IV with a compound of the formula V:

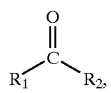
(V)

wherein $R_1$ and $R_2$ are as defined above, and chloroform in the presence of a base to give the compound of the formula II:

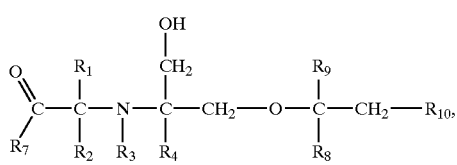
(II)

wherein $R_7$ is as defined above, and then
f) for obtaining a compound of the formula II wherein $R_3$ is different from hydrogen, reacting the compound of the formula II, wherein $R_3$ is hydrogen, with an alkylation reagent in case of step d) being not present; and then
g) reacting this compound of the formula II with a compound of the formula III:

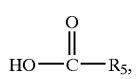
(III)

wherein $R_5$ is as defined above; and then
h) for obtaining a compound of the formula I wherein $R_3$ is different from hydrogen, reacting the compound of the formula I, wherein $R_3$ is hydrogen, with an alkylation reagent in case of steps d) and f) being not present.

Preferred reaction conditions for this process are as follows:

The reaction of step a) may be carried out at an elevated temperature, especially at temperatures of from 40 to 100° C., preferably of from 50 to 70° C., e.g. from 55 to 75° C.

Preferred bases of step a) are for example metal hydroxides like for example sodium hydroxide, potassium hydroxide or calcium hydroxide.

The formaldehyde in step a) is preferably used in at least twice molar amount in respect to the compound of the formula VI. Of interest is therefore a molar ratio between the compound of the formula VI and formaldehyde of 1:5 to 1:2; especially 1:4 to 1:2, for example 1:3 to 1:2. Preferably, a solvent like for example toluene is used.

The reaction of step b) may be carried out at an elevated temperature, especially at temperatures of from 50 to 120° C., preferably of from 70 to 100° C, e.g. from 85 to 95° C. Preferably, the reaction of step b) may be carried out in a solvent like for example toluene in an autoclave under pressure.

Preferred catalysts of step b) are for example acids like for example p-toluenesulfonic acid, sodium bisulfate [$NaHSO_4$] or phosphoric acid [$H_3PO_4$].

The compounds of the formula VIII or IX in step b) are preferably used in at least equal molar amount in respect to the compound of the formula XII. Preferably, the compounds of the formula VIII or IX are also used as a solvent. Of interest is therefore a molar ratio between the compounds of the formula VIII or IX and the compound of the formula VII of 5:1 to 1:1; especially 4:1 to 1:1, for example 3:1 to 1:1.

The preferred reaction parameters for steps c), d), e), f), g) and h) have already been discussed in detail.

The compounds of the formula II are suitable for stabilizing organic materials against oxidative, thermal or light-induced degradation. Special attention is drawn to their excellent action as light stabilizers.

Illustrative examples of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or α-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or a-methylstyrene, for example styrene on polybutadien, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/ vinyl acetate or vinylidene chloride/vinyl acetate copolymers.
9. Polymers derived from α,β-unsaturated acids and derivatives thereof such as polyacrylates and polymethacrylates; polymethyl methacrylates, polyacrylamides and polyacrylonitriles, impact-modified with butyl acrylate.
10. Copolymers of the monomers mentioned under 9) with each other or with other unsaturated monomers, for example acrylonitrile/butadiene copolymers, acrylonitrile/alkyl acrylate copolymers, acrylonitrile/ alkoxyalkyl acrylate or acrylonitrile/vinyl halide copolymers or acrylonitrile/alkyl methacrylate/butadiene terpolymers.
11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.
12. Homopolymers and copolymers of cyclic ethers such as polyalkylene glycols, polyethylene oxide, polypropylene oxide or copolymers thereof with bisglycidyl ethers.
13. Polyacetals such as polyoxymethylene and those polyoxymethylenes which contain ethylene oxide as a comonomer; polyacetals modified with thermoplastic polyurethanes, acrylates or MBS.
14. Polyphenylene oxides and sulfides, and mixtures of polyphenylene oxides with styrene polymers or polyamides.
15. Polyurethanes derived from hydroxyl-terminated polyethers, polyesters or polybutadienes on the one hand and aliphatic or aromatic polyisocyanates on the other, as well as precursors thereof.
16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).
17. Polyureas, polyimides, polyamide-imides, polyetherimids, polyesterimids, polyhydantoins and polybenzimidazoles.
18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.
19. Polycarbonates and polyester carbonates.
20. Polysulfones, polyether sulfones and polyether ketones.
21. Crosslinked polymers derived from aldehydes on the one hand- and phenols, ureas and melamines on the other hand, such as phenolformaldehyde resins, urea/ formaldehyde resins and melamine/formaldehyde resins.
22. Drying and non-drying alkyd resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example epoxy acrylates, urethane acrylates or polyester acrylates.
25. Alkyd resins, polyester resins and acrylate resins crosslinked with melamine resins, urea resins, isocyanates, isocyanurates, polyisocyanates or epoxy resins.
26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/ EVA, PVC/ABS, PVC/MBS, PC/ABS, PBTP/ABS, PC/ASA, PC/PBT, PVC/CPE, PVC/acrylates, POM/ thermoplastic PUR, PC/thermoplastic PUR, POM/ acrylate, POM/MBS, PPO/HIPS, PPO/PA 6.6 and copolymers, PA/HDPE, PA/PP, PA/PPO, PBT/PC/ABS or PBT/PET/PC.

Further objects of the invention are therefore compositions comprising a) an organic material which is susceptible to oxidative, thermal or light-induced degradation, and b) at least one compound of the formula II.

The invention likewise comprises a method of stabilizing an organic material against oxidative, thermal and/or actinic degradation, which comprises adding to this material at least one compound of the formula II.

Of particular interest is the use of compounds of the formula II as stabilizers in synthetic organic polymers, reprographic, especially photographic material, coatings or cosmetic formulations, especially in thermoplastic polymers and corresponding compositions as well as in coating compositions. Thermoplastic polymers of most importance in present compositions are polyolefines and their copolymers, such as listed above under items 1–3, thermoplastic polyolefin (TPO), thermoplastic polyurethan (TPU), thermoplastic rubber (TPR), polycarbonate, such as in item 19 above, and blends, such as in item 28 above. Of utmost importance are polyethylene (PE), polypropylene (PP), polycarbonate (PC) and polycarbonate blends such as PC/ABS blends.

Some of the above compounds of the formula II are especially well suitable for grafting them onto organic polymers having suitable functional groups. These are mainly compounds of the formula II carrying a hydroxy or an ethylenic double bond.

The invention therefore also pertains to a process for grafting a compound of the formula II carrying a hydroxy or an ethylenic double bond onto a polymer carrying suitable functional groups.

Polymers having suitable functional groups for the reaction with the hydroxy compounds of formula II are mainly organic polymers containing carboxy, anhydride or epoxy groups. Vice versa, polymers containing hydroxy groups are suitable for reactive bonding with present compounds of the formula II, which contain a carboxy group.

Grafting is preferably effected by exposure to UV light (photografting). Polymers having suitable functional groups for the reaction with double bonds are mainly unsaturated organic polymers containing ethylene double bonds in the main chain or in side chains.

Grafting reactions can be carried out in close analogy to methods known in the art, e.g. to methods described In EP-A-0 526 399, pages 6–16, or to methods described in U.S. Pat. No. 5,189,084.

Modified polymers thus obtained are highly stable against deleterious effects of light, oxygen and heat. If they contain reactively bonded units of present formula II in a sufficient amount, e.g. in an amount of 0.1 to 10 g, especially 2 to 10 g units of the formula II on 100 g of the final polymer, these modified polymers themselves can be used as stabilizers.

Other materials to be stabilized with the novel compositions are recording materials. By such materials are meant, for example, those described in Research Disclosure 1990, 31429 (pages 474–480), or in GB-A-2 319 523 or DE-A-19750906, page 22, line 15, until page 105, line 32, for photographic reproduction and other reprographic techniques.

Of special importance is the stabilization of non-silver reprographic materials, for example, those for pressure-sensitive copying systems, microcapsule photocopier systems, heat-sensitive copier systems and ink-jet printing.

The novel recording materials feature an unexpectedly high quality, especially in terms of their light stability.

The novel recording materials have a structure which is known per se and which corresponds to the utility. They consist of a base, for example paper or plastic film, on which one or more coatings are applied. Depending on the type of material, these coats contain the suitable components required, in the case of photographic material for example silver halide emulsions, colour couplers, dyes and the like. The material intended especially for ink-Jet printing has a customary base on which there is an absorption layer suitable for ink. Uncoated paper can likewise be employed for ink-jet printing; in this case, the paper functions simultaneously as a base and has the absorbent for the ink. Suitable material for ink-jet printing is described, inter alia, in U.S. Pat. No. 5,073,448, the disclosure content of which is regarded as part of the present description.

The recording material can also be transparent, for example in the case of projection films.

The compound or compounds of the formula II can be incorprated into the material even in the course of manufacture; in papermaking, for example, by addition to the pulp. Another method of use is the spraying of the material with an aqueous solution of compound(s) of the formula II, or the addition thereof to the coating. Coatings for transparent recording materials for projection must not contain any light-scattering particles such as pigments or fillers.

The colour-binding coatings can contain further additives, for example antioxidants, light stabilizers (including UV absorbers or hindered amine light stabilizers which are not included among the novel compounds of formula II), viscosity improvers, brighteners, biocides and/or antistats.

The coating is usually prepared as follows:

The water-soluble components, for example the binder, are dissolved in water and mixed. The solid components, for example fillers and other additives as already described, are dispersed in this aqueous medium. Dispersion is advantageously brought about with the aid of equipment such as ultrasonic devices, turbine agitators, homogenizers, colloid mills, bead mills, sand mills, high-speed stirrers and the like. A particular advantage of the compounds of the formula II is their ease of incorporation into the coating.

As mentioned, the novel recording materials cover a broad field of use. Compounds of the formula II can be employed, for example, in pressure-sensitive copier systems. They can be added to the paper to protect the microencapsulated dye precursors against light, or to the binder of the developer layer for protecting the dyes formed therein.

Photocopier systems with light-sensitive microcapsules which are developed by pressure are described, inter alia, in U.S. Pat. Nos. 4,416,966; 4,483,912; 4,352,200; 4,535,050; 4,365,463; 4,551,407; 4,562,137 and 4,608,330; and also in EP-A-0 139 479; EP-A-0 162 664; EP-A-0 164 931; EP-A-0 237 024; EP-A-0 237 025 and EP-A-0 260 129. In all these systems the compounds of the formula II can be added to the colour-accepting layer. Alternatively, the compounds of the formula II can be added to the donor layer for protecting the colour formers against light.

The compounds of the formula II can also be employed in recording materials which are based on the principle of photopolymerization, photosoftening or the rupture of microcapsules, or when heat-sensitive or photosensitive diazonium salts, leuco dyes with oxidizing agent or colour lactones with Lewis acids are used.

Heat-sensitive recording material exploits the colour-imparting reaction between a colourless or weakly coloured base dye and an organic or inorganic colour developer, the recorded image being produced by heat-induced contact of the two materials. This type of heat-sensitive recording material is very widespread, not only as the recording medium for faxes, computers, etc., but also in many other fields, for example in label printing.

The heat-sensitive recording material according to the present invention is composed of a base, a heat-sensitive colour-forming recording layer on this base, and, optionally, a protective layer on the heat-sensitive, colour-forming recording layer. The heat-sensitive, colour-forming recording layer contains as its principal constituent a colour-imparting compound and a colour-developing compound, and also a compound of the formula II. If the said protective layer is present, the compound of the formula II can also be incorporated into the protective layer.

Heat-sensitive recording materials are described, for example, in JP-A 8-267 915.

Further fields of use are recording materials for dye diffusion transfer printing, thermal wax transfer printing and dot matrix printing, and for use with electrostatic, electrographic, electrophoretic, magnetographic and laser-electrophotographic printers, recorders or plotters. Of the materials mentioned, preference is given to recording materials for dye diffusion transfer printing, as are described, for example, in EP-A-0 507 734.

Compounds of the formula II can also be employed in inks, preferably for ink-jet printing, for example those as described in U.S. Pat. No. 5,098,477, the disclosure content of which is regarded as part of the present description. The invention therefore also provides an ink comprising at least one compound of the formula II as stabilizer. The ink, especially for ink-jet printing, contains preferably water. Inks contain the stabilizer of the formula II usually in a concentration of from 0.01 to 20% by weight, in particular from 0.5 to 10% by weight.

The novel recording materials, for example photographic recording materials, also offer the advantage over materials comprising conventional HALS that the stabilizers of the formula II are required in a comparatively small amount, meaning also that the thickness of the stabilizer-containing layer remains low, a factor which has a positive effect, inter alia, on the imaging properties. Another advantage of the novel stabilizers is their heightened inherent stability under extreme climatic conditions, especially at high humidity and high temperature. The novel photographic material can be a black and white or a colour photographic material; colour photographic material is preferred.

Examples of colour photographic materials are colour negative films, colour reversal films, colour positive films, colour photographic paper, colour reversal photographic paper, colour-sensitive materials for the dye diffusion transfer process or the silver dye bleach process. Details of the photographic material to be stabilized according to the invention and components which can be employed in the novel material are given, inter alia, in GB-A-2 319 523, DE-A-19 750 906, page 23, line 20, until page 105, line 32, and in U.S. Pat. No. 5,538,840, column 25, line 60, to column 106, line 31; these parts of U.S. Pat. No. 5,538,840 are incorporated herein by way of reference.

The compounds of the invention are also valuable light stabilizers in cosmetic, pharmaceutical or veterinary formulations. The substrate to be protected in these applications may be the formulation itself or components thereof, or human or animal skin or hair. The compounds of the invention may be used in dissolved or micronized state. The invention therefore also pertains to a cosmetic formulation containing at least one compound of the formula II and cosmetically acceptable carriers or auxiliary agents. A more detailed description of the cosmetic formulations which can be stabilized according to the invention can be found in GB-A-2 319 523.

The organic polymeric materials to be protected are preferably natural, semisynthetic or, preferably, synthetic organic materials. Particular preference is given to synthetic organic polymers or mixtures of such polymers, especially thermoplastic polymers such as polyolefins, especially polyethylene and polypropylene (PP), and coating compositions.

In general the compounds of the formula II are added to the material to be stabilized in amounts of from 0.1 to 10%, preferably from 0.01 to 5%, In particular from 0.01 to 2% (based on the material to be stabilized). Particular preference is given to the use of the novel compounds in amounts of from 0.05 to 1.5%, especially from 0.1 to 0.5%.

Incorporation into the materials can be effected, for example, by mixing in or applying the compounds of the formula II and, if desired, further additives by the methods which are customary in the art. Where polymers are involved, especially synthetic polymers, incorporation can take place prior to or during the shaping operation, or by applying the dissolved or dispersed compound to the polymer, with or without subsequent evaporation of the solvent. In the case of elastomers, these can also be stabilized as latices. A further possibility for incorporating the compounds of the formula II into polymers is to add them before, during or directly after the polymerization of the corresponding monomers or prior to crosslinking. In this context the compound of the formula II can be added as it is or else in encapsulated form (for example in waxes, oils or polymers). In the case of addition prior to or during the polymerization, the compounds of the formula II can also act as a regulator of the chain length of the polymers (chain terminator).

The compounds of the formula II can also be added in the form of a masterbatch containing said compound in a concentration, for example, of from 2.5 to 25% by weight to the polymers that are to be stabilized.

The compounds of the formula II can judiciously be incorporated by the following methods:
- as emulsion or dispersion (e.g. to latices or emulsion polymers),
- as a dry mixture during, the mixing in of additional components or polymer mixtures,
- by direct introduction into the processing apparatus (e.g. extruders, internal mixers, etc),
- as solution or melt.

Novel polymer compositions can be employed in various forms and/or processed to give various products, for example as (to give) films, fibres, tapes, moulding compositions, profiles, or as binders for coating materials, adhesives or putties.

In addition to the compounds of the formula II the novel compositions may as additional component c) comprise one or more conventional additives such as, for example, those indicated below.

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4methylphenol, 2,4-dimethyl-6-(1'-methylundec-1'-yl) phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4- hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butylhydroxybenzyl)isocyanurate, 1,3,5-tris(4-tert-butyl-3-hydroxy-2,6-dimethylbenzyl)isocyanurate, 2,4,6-tris-(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)iso cyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecarol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane.

1.15. Esters of β-(3.5-dicyclohexyl-4-hydroxyphenyl) pronionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hyaroxyphenyl]propionyloxy)ethyl]oxamide (Naugard®XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyidiphenylamines, a mixture of mono- and dialkylated nonyidiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine; phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene.

2. UV Absorbers and Light Stabilizers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$, where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)phenyl]-benzotriazole; 2-[2'-hydroxy-3'-(1,1,3,3-tetramethylbutyl)-5'-(α,α-dimethylbenzyl)phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for xample 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-Cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl)n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpipefidyl)-2-n-butyl-2-(2-hydroxy-3,5-di-tert-butylbenzy)-malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine-4-yl)-N-butyl-amino]-6-(2-hydroxyethyl)amino-1,3,5-triazine.

2.7. Oxamides, for example 4,4'-dioctyloxyoxanilide, 2,2'-diethoxyoxanilide, 2,2'-dioctyloxy-5,5'-di-tertbutoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosohites and phosphonites, for example triphenyl phosphite, diphenylalkyl phosphites, phenyldialkyl phosphites, tris(nonylphenyl)phosphite, trilauryl phosphite, trioctadecyl phosphite, distearylpentaerythritol diphosphite, tris(2,4-di-tert-butylphenyl)phosphite, diisodecyl pentaerythritol diphosphite, bis(2,4-di-tert-butylphenyl) pentaerythritol diphosphite, bis(2,4-dicumylphenyl) pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl)methyl phosphite, bis(2,4-di-tert-butyl-6-methylphenyl)ethyl phosphite, 6-fluoro-2,4,8,10-tetra-tert-butyl-12-methyl-dibenz[d,g]-1,3,2-dioxaphosphocin, 2,2',2''-nitrilo-[triethyltris(3,3',5,5'-tetra-tert-butyl-1,1'-biphenyl-2,2'-dlyl)phosphite], 2-ethylhexyl (3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example N-benzyl-alpha-phenylnitrone, N-ethlyl-alpha-methylnitrone, N-octyl-alpha-heptylnitrone, N-lauryl-alpha-undecylnitrone, N-tetradecyl-alpha-tridecyinitrone, N-hexadecyl-alpha-pentadecyinitrone, N-octadecyl-alpha-heptadecyinitrone, N-hexadecyl-alpha-heptadecyinitrone, N-ocatadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene) sorbitol, 1,3:2,4-di(paramethyldibenzylidene)sorbitol, and 1,3:2,4-di(benzylidene)sorbitol.

12. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. Nos. 4,325,863; 4,338,244; 5,175,312; 5,216,052; 5,252,643; DE-A-4316611; DE-A-4316622; DE-A-4316876; EP-A-0589839 or EP-A-0591102 or 3-[4-(2-acetoxyethoxy)phenyl]-5,7-di-tert-butylbenzofuran-2-one, 5,7-di-tert-butyl-3-[4-(2-stearoyloxyethoxy)phenyl]-benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tertbutylbenzofuran-2-one, 3-(2,3-dimethylphenyl)-5,7-di-tert-butylbenzofuran-2-one.

The conventional additives are typically used in concentrations of 0.01 to 10%, based on the total weight of the material to be stabilized.

The novel compounds of the formula V can be used in particular together with phenolic anti-oxidants, light stabilizers, processing stabilizers, solvents, pigments, dyes, plasticizers, thixotropic agents, levelling assistants, further light stabilizers and/or metal passivators.

Other preferred compositions comprise, in addition to compounds of the formula II, a stabilizer selected from the class of the 2-hydroxyphenyl-triazines and/or 2-hydroxyphenyl-benzotriazoles.

Likewise of particular interest is the use of the novel mixtures comprising compounds of the formula II as stabilizers for coatings, for example for paints. The invention therefore also relates to those compositions whose component (a) is a film-forming binder for coatings.

The novel coating composition preferably comprises 0.01–10 parts by weight of (b), in particular 0.05–10 parts by weight of (b), especially 0.1–5 parts by weight of (b), per 100 parts by weight of solid binder (a).

Multilayer systems are possible here as well, where the concentration of the novel stabilizer [component (b)] in the outer layer can be relatively high, for example from 1 to 15 parts by weight of (b), in particular 3–10 parts by weight of (b), per 100 parts by weight of solid binder (a).

The use of the novel stabilizers in coatings is accompanied by the additional advantage that it prevents delamination, i.e. the flaking-off of the coating from the substrate. This advantage is particularly important in the case of metallic substrates, including multilayer systems on metallic substrates.

The binder [component (a)] can in principle be any binder which is customary in industry, for example those described in Ullmann's Encyclopedia of Industrial Chemistry, 5th Edition, Vol. A18, pp. 368–426, VCH, Weinheim 1991. In general, it is a film-forming binder based on a thermoplastic or thermosetting resin, predominantly on a thermosetting resin. Examples thereof are alkyd, acrylic, polyester, phenolic, melamine, epoxy and polyurethane resins and mixtures thereof.

Component (a) can be a cold-curable or hot-curable binder; the addition of a curing catalyst may be advantageous. Suitable catalysts which accelerate curing of the binder are described, for example, in Ullmann's Encyclopedia of Industrial Chemistry, Vol. A18, p. 469, VCH Verlagsgesellschaft, Weinheim 1991.

Preference is given to coating compositions in which component (a) is a binder comprising a functional acrylate resin and a crosslinking agent.

Examples of coating compositions containing specific binders are:
1. Paints based on cold- or hot-crosslinkable alkyd, acrylate, polyester, epoxy or melamine resins or mixtures of such resins, if desired with addition of a curing catalyst.
2. Two-component polyurethane paints based on hydroxyl-containing acrylate, polyester or polyether resins and aliphatic or aromatic isocyanates, isocyanurates or polyisocyanates.
3. One-component polyurethane paints based on blocked isocyanates, isocyanurates or polyisocyanates which are deblocked during baking, if desired with addition of a melamine resin.
4. One-component polyurethane paints based on a tris-alkoxycarbonyltriazine crosslinker and a hydroxyl group containing resin such as acrylate, polyester or polyether resins.
5. One-component polyurethane paints based on aliphatic or aromatic urethaneacrylates or polyurethaneacrylates having free amino groups within the urethane structure and melamine resins or polyether resins, if necessary with curing catalyst.
6. Two-component paints based on (poly)ketimines and aliphatic or aromatic isocyanates, isocyanurates or polyisocyanates.
7. Two-component paints based on (poly)ketimines and an unsaturated acrylate resin or a polyacetoacetate resin or a methacrylamidoglycolate methyl ester.
8. Two-component paints based on carboxyl- or amino-containing polyacrylates and polyepoxides.
9. Two-component paints based on acrylate resins containing anhydride groups and on a polyhydroxy or polyamino component.
10. Two-component paints based on acrylate-containing anhydrides and polyepoxides.
11. Two-component paints based on (poly)oxazolines and acrylate resins containing anhydride groups, or unsaturated acrylate resins, or aliphatic or aromatic isocyanates, isocyanurates or polyisocyanates.
12. Two-component paints based on unsaturated polyacrylates and polymalonates.
13. Thermoplastic polyacrylate paints based on thermoplastic acrylate resins or externally crosslinking acrylate resins in combination with etherified melamine resins.
14. Paint systems based on siloxane-modified or fluorine-modified acrylate resins.

In addition to components (a) and (b), the coating composition according to the invention preferably comprises as component (c) a light stabilizer of the sterically hindered amine type, the 2-(2-hydroxyphenyl)-1,3,5-triazine and/or 2-hydroxyphenyl-2H-benzotriazole type, for example as mentioned in the above list in sections 2.1, 2.6 and 2.8. Further examples for light stabilizers of the 2-(2-hydroxyphenyl)-1,3,5-triazine type advantageously to be added can be found e.g. in the publications U.S. Pat. No. 4,619,956, EP-A-0 434 608, U.S. Pat. Nos. 5,198,498; 5,322,868; 5,369,140; 5,298,067, WO-A-94/18278, EP-A-0 704 437, GB-A-2 297 091, WO-A-96/28431. Of special technical interest is the addition of the 2-(2-hydroxyphenyl)-1,3,5-triazines and/or 2-hydroxyphenyl-2H-benzotriazoles, especially the 2-(2-hydroxyphenyl)-1,3,5-triazines.

To achieve maximum light stability, it is of particular interest to add sterically hindered amines as set out in the abovementioned list under 2.6. The invention therefore also relates to a coating composition which in addition to components (a) and (b) comprises as component (c) a light stabilizer of the sterically hindered amine type.

The novel coating compositions can also be radiation-curable coating compositions. In this case, the binder essentially comprises monomeric or oligomeric compounds containing ethylenically unsaturated bonds, which after application are cured by actinic radiation, i.e., converted into a crosslinked, high molecular weight form. Where the system is UV-curing, it generally contains a photoinitiator as well. Corresponding systems are described in the above-mentioned publication Ullmann's Encyclopedia of Industrial Chemistry, 5th Edition, Vol. A18, pages 451–453. In radiation-curable coating compositions, the novel stabilizers can also be employed without the addition of sterically hindered amines.

The coating compositions according to the invention can be applied to any desired substrates, for example to metal, wood, plastic or ceramic materials. They are preferably used as topcoat in the finishing of automobiles. If the topcoat comprises two layers, of which the lower layer is pigmented and the upper layer is not pigmented, the novel coating composition can be used for either the upper or the lower layer or for both layers, but preferably for the upper layer.

The novel coating compositions can be applied to the substrates by the customary methods, for example by brushing, spraying, pouring, dipping or electrophoresis; see also Ullmann's Encyclopedia of Industrial Chemistry, 5th Edition, Vol. A18, pp. 491–500.

Depending on the binder system, the coatings can be cured at room temperature or by heating. The coatings are preferably cured at 50–150° C., and in the case of powder coatings or coil coatings even at higher temperatures.

The coatings obtained in accordance with the invention have excellent resistance to the damaging effects of light, oxygen and heat; particular mention should be made of the good light stability and weathering resistance of the coatings thus obtained, for example paints.

The invention therefore also relates to a coating, in particular a paint, which has been stabilized against the damaging effects of light, oxygen and heat by a content of the compound of the formula II according to the invention. The paint is preferably a topcoat for automobiles. The invention furthermore relates to a process for stabilizing a coating based on organic polymers against damage by light, oxygen and/or heat, which comprises mixing with the coating composition a mixture comprising a compound of the formula II, and to the use of mixtures comprising a compound of the formula II in coating compositions as stabilizers against damage by light, oxygen and/or heat.

The coating compositions can comprise an organic solvent or solvent mixture in which the binder is soluble. The coating composition can otherwise be an aqueous solution or dispersion. The vehicle can also be a mixture of organic solvent and water. The coating composition may be a high-solids paint or can be solvent-free (e.g. a powder coating material). Powder coatings are, for example, those described in Ullmann's Encyclopedia of Industrial Chemistry, 5th Ed., A18, pages 438–444. The additive of present invention can be used therein e.g. as described e.g. in EP-A-856563, especially page 22, line 21, until page 26, line 29, and literature cited in this reference. The powder coating material may also have the form of a powder-slurry (dispersion of the powder preferably in water).

Examples of resins for powder coatings are:
1. Carboxy- or hydroxy-functionalised polyester resins, based on monomers such as terephthalic acid, isophthalic acid, neopentyl glycol, 2-methyl-1,3-propandiol, tris-1,1,1-(hydroxymethyl)propane etc.
2. Epoxy resins based on bisphenols, such as bisphenol A or Novolac® epoxy resins for thermal or uv-cure with cationic photoinitiators.
3. Hydroxy-, carboxy- or glycidyl-functionalised acrylate polymers and copolymers. Suitable comonomers include styrene, alkyl methacrylates, acrylamide, acrylonitrile etc.
4. Unsaturated polyester resins for uv-cureable powder coatings, typically used in conjunction with multifuntlonal vinyl ethers or acrylate esters.

Powder coating based on resins with carboxy functionality are typically used together with crosslinking agents of the following classes:
1) Polyfunctional epoxy compounds, such as epoxy resins, triglycidylisocyanurate, epoxidised unsaturated fatty acid esters (such as Uranox® resins from DSM), and esters and ethers of glycidol (such as Araldit® PT910 from Ciba Specialty Chemicals).
2) β-Hydroxyalkylamides, such as Primi® types XL552 and QM1260 from Ems Chemie.
3) Derivatives of melamine, benzoguanimine and glycoluril, such as Powderlink® 1174 from American Cyanamid.

Crosslinking agents for resins of hydroxy functionality include anhydrides and especially blocked diisocyanates and uretdiones, etc.

Powder coatings based on resins with epoxy functionality are typically used together with crosslinking agents such as diacids (such as 1,12-dodecanedioic acid), carboxy-functional polyesters, carboxy-functional copolymers of acrylates and methacrylates, anhydrides (such as the anhydride prepared from 1,12-dodecanedioic acid).

Other additives that can be used together with the compounds of the invention in powder coatings include: degassing agents, flow promoters, tribocharging additives cure catalysts, sensitisers, cationic and free-radical photoinitiators, as well as typical liquid paint additives.

A particular advantage of the compounds of the formula II is their low basicity, as basic compounds often catalyse the crosslinking reactions of powder coatings to cause poor flow and degassing, and reduced storage stability. This is particularly useful in formulations of high reactivity, such as the glycidylmethacrylate-functionalised acrylics. Here, the combination of the compounds of the invention together with uv-absorbers, especially of the hydroxyphenyltriazine class, can be used to improve the weatherability without causing catalysis. In other binder systems and with other classes of uv-absorbers, such as those previously mentioned to be of particular use in automotive paints, synergistic effects on the weatherability are also found.

In powder coatings the compounds of the invention can also be used to improve the oxidative stability and reduce yellowing on curing and overbaking. Here not only is the low basicity advantageous, but also the ability of the hindered morpholinones to withstand and prevent yellowing caused by oxides of nitrogen in gas-fired ovens. Use together particularly with phosphite and phosphonite costabilizers, as disclosed in EP-A-0 816 442, and dialkylesters of dithiopropionic acid is particularly beneficial. The compounds of the invention can, where appropriate also be used to stabilise polyester during manufacture as well as at all stages of its subsequent use.

Likewise preferred is the use of the coating composition as a topcoat for applications in the automobile industry, especially as a pigmented or unpigmented topcoat of the paint finish. Its use for underlying coats, however, is also possible.

The pigments can be inorganic, organic or metallic pigments. The novel coating compositions preferably contain no pigments and are used as a clearcoat.

A preferred embodiment of this invention is therefore the use of a compound of the formula II as stabilizer for an organic materials against oxidative, thermal or light-induced degradation.

The invention also relates to a process for stabilizing an organic material against oxidative, thermal or light-induced degradation, which comprises incorporating therein or applying thereto at least one compound of the formula II.

The following Examples illustrate the invention further. Parts or percentages relate to weight.

EXAMPLE 1

Process for the Preparation of Compound 101,
Table 1 a) Preparation of 2-nitro-propan-1-ol.

To a solution of 11.4 g (0.38 mol) of paraformaldehyde in 250 g (3.33 mol) of nitroethane, is added 0.3 g (7.5 mmol) of sodium hydroxide. The reaction mixture is maintained at 70° C. for two hours. The reaction mixture is then cooled to room temperature, filtered and the filtrate concentrated using a vacuum rotary evaporator. The residue yields crude 2-nitro-propan-1-ol.

b) Preparation of 1-tert-butoxy-2-nitro-propane.

To a solution of 36.6 g (0.34 mol) of crude 2-nitro-propan-1-ol [prepared according to Example 1a]in 200 ml of toluene in a pressure vessel is added 2 g of sodium bisulfate [NaHSO$_4$]. Through the closed autoclave is added at room temperature 48 g (0.85 mol) of isobutene. The reaction mixture is maintained at 60° C. for 8 hours. The reaction mixture is cooled to room temperature, diluted with toluene and filtered to give a crude solution of 1-tert-butoxy-2-nitro-propane in toluene.

c) Preparation of 3-tert-butoxy-2-methyl-2-nitro-propan-1-ol.

To the crude solution of 1-tert-butoxy-2-nitro-propane in toluene according to Example 1b is added 12.1 g (0.4 mol) of paraformaldehyde and 1 g of sodium hydroxide. The reaction mixture is maintained at 70° C. for two hours. The reaction mixture is then cooled to room temperature, filtered and the filtrate concentrated using a vacuum rotary evaporator. The residue yields crude 3-tert-butoxy-2-methyl-2-nitro-propan-1-ol as a yellow powder.

c') Alternative one pot synthesis of 3-tert-butoxy-2-methyl-2-nitro-propan-1-ol.

A stirred solution of 140 g (1.87 mol) of nitroethane, 116 g (3.87 mol) of paraformaldehyde and 0.5 g of sodium hydroxide in 1200 ml of toluene in an autoclave is heated to 60–65° C. and maintained at this tempereature for 2 hours. The reaction mixture is cooled to room temperature and treated with 15 g of phosphoric acid [H$_3$PO$_4$]. The pressure vessel is closed again and 135 g (2.4 mol) of isobutene is added. The reaction is heated to 90° C. and maintained at this temperature for one hour under stirring. The stirring was then stopped at 90° C.; after 30 minutes the phosphoric layer at the bottom of the autoclave was separated and the temperature was decreased to room temperature. The mixture was diluted with toluene, filtered and the filtrate concentrated using a vacuum rotary evaporator. The residue yields crude 3-tert-butoxy-2-methyl-2-nitro-propan-1-ol as a yellow powder.

d) Preparation of 2-amino-3-tert-butoxy-2-methyl-propan-1-ol (compound 301, Table 1).

To a solution of 150 g (0.78 mol) of 3-tert-butoxy-2-methyl-2-nitro-propan-1-ol [prepared according to Example 1c or 1c'] in 700 ml of toluene in a pressure vessel is added 15 g of Raney-Ni and 40 ml of a pH 7.00 buffer [NORMEX (RTM), Carlo Erba]. Through the closed autoclave is added at room temperature hydrogen under 50–60 bar pressure. The reaction mixture is heated to 40° C. and maintained at this temperature for 8 hours. The reaction mixture is then cooled to room temperature, diluted with toluene, filtered and the filtrate concentrated using a vacuum rotary evaporator. The residue yields 2-amino-3-tert-butoxy-2-methyl-propan-1-ol (compound 301, Table 1), pale green solid, m.p. 30–35° C.

In analogy to Examples 1a, 1b, 1c and 1d starting from 1-nitro-propane instead of nitro-ethane, 2-amino-3-tert-butoxy-2-ethyl-propan-1-ol (compound 302, Table 1), boiling point 156° C. at 0.3 mm Hg, is obtained.

e) Preparation of sodium salt of 2-(2-tert-butoxy-1-hydroxymethyl-1-methyl-ethylamino)-2-methyl-propionic acid (compound 201, Table 1).

To a solution of 45 g (0.27 mol) of 2-amino-3-tert-butoxy-2-methyl-propan-1-ol [compound 301, Table 1, prepared according to Example 1 d] and 62 g (0.52 mol) of chloroform in 400 g of acetone is added in portions of 5 g every 5 minutes a total amount of 62 g (1.55 mol) of sodium hydroxide. The reaction is stirred at room temperature for additional 6 hours and then filtered. The residue is washed with acetone and dried under vacuum to give the sodium salt of 2-(2-tert-butoxy-1-hydroxymethyl-1-methyl-ethylamino)-2-methyl-propionic acid (compound 201, Table 1) which contains approximately 57.6% of sodium chloride.

f) Preparation of Compound 101, Table 1.

A suspension of 14.6 g sodium salt of 2-(2-tert-butoxy-1-hydroxymethyl-1-methyl-ethylamino)-2-methyl-propionic acid [compound 201, Table 1, prepared according to Example 1e] which contains approximately 57.6% of sodium chloride; 6.64 g of 2-ethyl-hexanoic acid; 22 g petroleum in the boiling range of 160–180° C.; 0.47 g of tin(II)oxide and 3.5 g of hydrochloric acid (32 wt. % in water) is heated up slowly to 180° C. The formed water and tert-butanol is continuously removed by azeotropic distillation into a Dean-Stark trap returning the petroleum to the reaction mixture. When the reaction is complete [measured by $^1$H-NMR] the mixture is cooled to room temperature, filtered and the filtrate concentrated using a vacuum rotary evaporator. The residue Is dissolved at room temperature in 40 ml hexane and separated from the insoluble parts by filtration. The hexane solution is treated with 3.3 g of sodium carbonate [Na$_2$CO$_3$] and stirred at room temperature for 30 minutes. Then 30 ml of water is added and after another 20 minutes of stirring at room the temperature the organic phase is separated from the aqueous phase. The organic phase is washed with water, dried over sodium sulfate and concentrated using a vacuum rotary evaporator. The residue yields 5.68 g (82%) of compound 101, Table 1.

EXAMPLE 2

Process for the Preparation of Compound 101, Table 1

A suspension of 14.6 g sodium salt of 2-(2-tert-butoxy-1-hydroxymethyl-1-methyl-ethylamino)-2-methyl-propionic acid [compound 201, Table 1, prepared according to Example 1e] which contains approximately 57.6% of sodium chloride; 6.64 g of 2-ethyl-hexanoic acid; 22 g petroleum in the boiling range of 160–180° C.; 0.47 g of tin(II) 2-ethylhexanoate and 3.5 g of hydrochloric acid (32 wt. % in water) is heated up slowly to 180° C. The formed water and tert-butanol is continuously removed by azeotropic distillation into a Dean-Stark trap returning the petroleum to the reaction mixture. While holding at 180° C. another 3.0 g of hydrochloric acid (32 wt. % in water) is added in two portions. When the reaction is complete [measured by $^1$H-NMR] the mixture is cooled to room temperature, filtered and the filtrate concentrated using a vacuum rotary evaporator. The residue is dissolved at room temperature in 40 ml hexane and separated from the insoluble parts by filtration. The hexane solution is treated with 3.3 g of sodium carbonate [Na$_2$CO$_3$] and stirred at room temperature for 30 minutes. Then 30 ml of water is added and after another 15 minutes of stirring at room the temperature the organic phase is separated from the aqueous phase. The organic phase is washed with water, dried over sodium sulfate and concentrated using a vacuum rotary evaporator. The residue yields 5.67 g (82%) of compound 101, Table 1. 3.027 g of the crude product are Kugelrohr distilled at 150° C. and 0.45 mbar yielding 2.12 g of compound 101, Table 1. Assay by HPLC: 97%. Transmittance at 500 nm of a 10% solution of compound 101 in ethylacetate is 97%.

EXAMPLE 3

Process for the Preparation of Compound 101, Table 1

A suspension of 14.6 g sodium salt of 2-(2-tert-butoxy-1-hydroxymethyl-1-methyl-ethylamino)-2-methyl-propionic acid [compound 201, Table 1, prepared according to Example 1 e] which contains approximately 57.6% of sodium chloride; 6.64 g of 2-ethyl-hexanoic acid; 22 g petroleum in the boiling range of 160–180° C.; 0.16 g of tin(II)oxide; 1.59 g of hypophosphorous acid [$H_3PO_2$] and 2.35 g of sulfuric acid (96 wt. %) is heated up slowly to 180° C. The formed water and tert-butanol is continuously removed by azeotropic distillation into a Dean-Stark trap, returning the petroleum to the reaction mixture. When the reaction is complete [measured by $^1$H-NMR] the mixture is cooled to room temperature, filtered and the filtrate concentrated using a vacuum rotary evaporator. The residue is dissolved at room temperature in 30 ml hexane and separated from the insoluble parts by filtration. The hexane solution is treated with 4 g of sodium carbonate [$Na_2CO_3$] and stirred at room temperature for 30 minutes. Then 30 ml of water is added and after another 30 minutes of stirring at room the temperature the organic phase is separated from the aqueous phase. The organic phase is washed with water, dried over sodium sulfate and concentrated using a vacuum rotary evaporator. The residue yields 5.66 g (82%) of compound 101, Table 1.

EXAMPLE 4

A solution of 20 g sodium salt of 2-(2-tert-butoxy-1-hydroxymethyl-1-methyl-ethylamino)-2-methyl-propionic acid [compound 201, Table 1, prepared according to Example 1e] which contains approximately 57.6% of sodium chloride; in 62 ml of water and 7 ml of hydrochloric acid (37 wt. % in water) is refluxed for two hours. The formed tert-butanol is distilled off. The reaction mixture is cooled to 40° C. and treated with 36 ml of water and 5 ml of a 30% solution of sodium hydroxide to give a pH of is 7–8. The reaction mixture is refluxed for an additional hour. Then 46 ml of toluene is added and the water distilled off azeotropically. Afterwards 84.2 ml of 2 ethyl-hexanoic acid, 0.22 g of p-toluenesulfonic acid and 5 ml toluene is added. The reaction mixture is heated at 215–220° C. for 4 hours. The excess of 2-ethyl-hexanoic acid is distilled off. The residue is diluted with hexane and then washed twice with a solution of sodium carbonate. The organic phase is dried over sodium sulfate and concentrated using a vacuum rotary evaporator. The residue yields 7.78 g (82%) of compound 101, Table 1.

TABLE 1

| No. | Compound |
|---|---|
| 101 | (structure: morpholinone with N–H, two CH$_3$ groups on ring carbon, CH$_2$–O–C(=O)–CH(CH$_2$CH$_3$)–CH$_2$CH$_2$CH$_2$CH$_3$) |
| 201 | (structure: Na$^+$ $^-$O–C(=O)–C(CH$_3$)$_2$–N(H)–C(CH$_3$)$_2$–CH$_2$–O–C(CH$_3$)$_3$ with OH on CH$_2$) |
| 301 | H$_2$N–C(CH$_3$)(CH$_2$OH)–CH$_2$–O–C(CH$_3$)$_3$ |
| 302 | H$_2$N–C(CH$_2$CH$_3$)(CH$_2$OH)–CH$_2$–O–C(CH$_3$)$_3$ |

EXAMPLE 5

Light-stabilizing Action in Polyproplylene Tapes 1 g of each of the compounds listed in the following Table 2, 1 g of tris(2,4-di-tert-butylphenyl)phosphite, 0.5 g of pentaerythritol tetrakis[3-(3,5-di-tert-butyl-4-hydroxyphenyl)propionate] and 1 g of calcium stearate are mixed in a turbomixer with 1 kg of polypropylene powder having a melt index of 3.7 (measured at 230° C. and 2,16 kg). The mixtures are extruded at 200–220° C. to give polymer granules which are subsequently converted to streched tapes of 50 μm thickness and 2.5 mm width using a semi-industrial type of apparatus [Leonard-Sumirago (RTM)] and working under the following conditions: Extruder temperature: 210–230° C.; Head temperature: 240–26000; and Stretch ratio: 1:6.

The tapes thus prepared are mounted on a white card and exposed in a Weather-O-Meter 65 WR (ASTM D 2565-85) with a black panel temperature of 63° C. The residual tenacity is measured, by means of a constant velocity tensometer, on a sample taken after various light exposure times; from this, the exposure time in hours required to halve the initial tenacity ($T_{50}$) is measured. The higher the value the better is the polypropylene tape stabilized. By way if comparison, tapes prepared under the same conditions as indicated above, but without the addition of the stabilizers of the present invention are exposed. The results are summarized in Table 2.

TABLE 2

| Example | Stabilizer | $T_{50}$ (hours) |
|---|---|---|
| 5a[a] | — | 500 |
| 5b[b] | Compound 201 | 1930 |

[a]Comparison Example.
[b]Example of this invention.

EXAMPLE 6

Measuring the Discoloration of Powder Coatings Based on a Carboxy-functional Polyester and Cured in Electric and Gas Ovens To prepare the powder coating composition based on a carboxy-functional polyester, components 1 to 6

(formulation without additives) or components 1 to 7 (formulation containing the stabilizers) are employed in the sequence indicated (cf. Table 3).

TABLE 3

| Components | Examples (amount in grams) | |
|---|---|---|
| | 6a, d | 6b, c, e, f |
| 1. Crylcoat ® 360[c] | 591 | 591 |
| 2. Araldit ® GT 7004[d] | 394 | 394 |
| 3. Octadecyltrimethylammonium bromide[e] | 3.6 | 3.6 |
| 4. Resiflow ® PV 88[f] | 12 | 12 |
| 5. Benzoin[g] | 3 | 3 |
| 6. Titanium dioxide type R-KB-5[h] | 500 | 500 |
| 7. Stabilizers (see Tables 4 and 5) | — | 9 |
| Total: | 1503.6 | 1512.6 |

[c]Crylcoat ® 360 polyester resin from UCB S.A., Drogenbos, Belgium.
[d]Araldit ® GT 7004 (Ciba Specialty Chemicals Inc.) is a bisphenol A diglycidyl ether.
[e]Octadecyltrimethylammonium bromide from Fluka AG, Buchs, Switzerland.
[f]Resiflow ® PV 88 silicon free acrylate levelling assistant from Worlée Chemie GmbH, Lauenburg, Germany.
[g]Benzoin from Fluka AG.
[h]Titanium dioxide type R-KB-5 from Bayer AG, Leverkusen, Germany.

The components weighed out in this way are mixed using a planetary stirrer. The mixture is then extruded on a prism extruder at 300 revolutions/minute and at 100° C. and is rolled out. The powder coating composition is coarsely comminuted using a bench cutter and is ground in a Retsch ZM-1 ultracentrifugal mill with a 0.75 mm annular-perforation screen at 15,000 revolutions/minute. Finally, the powder is passed through a 30 μm screen on a centrifugal screening machine.

The finished powder coating composition is sprayed electrostatically to a coat thickness of 70 lam onto aluminium panels using an ESB-Wagner corona cup gun at 60 kV. Some of the coated panels are cured at 180° C. for 90 minutes in an electric oven. The remaining coated panels are cured at 180° C. for 45 minutes in a gas oven with an $NO_2$ content of 20 ppm. The yellowness index (YI) of the samples is determined in accordance with ASTM D 1925-70. Low YI values denote little discoloration, high YI values denote severe discoloration of the samples. The less the discoloration, the more effective the stabilizer. The results are summarized in Tables 4 and 5.

TABLE 4

Curing for 90 minutes in an electric oven at 180° C.

| Example | Stabilizers (% rel. to components 1 to 5) | Yellowness index after 90 minutes (ASTM D 1925-70) |
|---|---|---|
| 6a[a] | — | 3.1 |
| 6b[b] | 0.60% Compound 201 | 2.8 |
| 6c[b] | 0.50% Irgafos ® 168[i] 0.10% Compound 201 | 2.8 |

For footnotes [a], [b] and [i] see the end of Table 5.

TABLE 5

Curing for 45 minutes in a gas oven at 180° C.

| Example | Stabilizers (% rel. to components 1 to 5) | Yellowness index after 90 minutes (ASTM D 1925-70) |
|---|---|---|
| 6d[a] | — | 4.2 |
| 6e[b] | 0.60% Compound 201 | 3.4 |
| 6f[b] | 0.50% Irgafos ® 168[i] 0.10% Compound 201 | 3.4 |

[a]Comparison Example.
[b]Example of this invention.
[i]Irgafos ® 168 (Ciba Specialty Chemicals Inc.) is tris(2,4-di-tert-butylphenyl)phosphite.

What is claimed is:

1. A process for the preparation of compounds of the formula I:

$$\text{(I)}$$

wherein $R_1$ and $R_2$ are each independently of the other $C_1$–$C_{18}$alkyl, $C_2$–$C_{18}$alkyl which is interrupted by oxygen or by $$\diagdown N - R_6;$$

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy; or $R_1$ and $R_2$, together with the carbon atom to which they are bonded, form a $C_5$–$C_8$cycloalkylidene ring unsubstituted or substituted by from 1 to 3 $C_1$–$C_4$alkyl groups;

$R_3$ is hydrogen, $C_1$–$C_{18}$alkyl, $C_2$–$C_{18}$alkyl which is interrupted by oxygen or by $$\diagdown N - R_6;$$

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy; $C_1$–$C_{12}$alkoxy, $C_5$–$C_{12}$cycloalkoxy, $C_2$–$C_{12}$alkenyloxy, $C_7$–$C_{12}$phenylalkoxy, $C_7$–$C_{12}$phenylalkoxy substituted by hydroxy, $C_1$–$C_4$alkyl and/or $C_1$–$C_4$alkoxy;

$R_4$ is $C_1$–$C_{18}$alkyl, $C_2$–$C_{18}$alkyl which is interrupted by oxygen or by $$\diagdown N - R_6;$$

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cydoalkyl, $C_5$–$C_{12}$cycloalkyl substituted by hydroxy, $C_1$–$C_4$alkyl and/or $C_1$–$C_4$alkoxy;

$R_5$ is $C_1$–$C_{18}$alkyl, $C_2$–$C_{18}$alkyl which is interrupted by oxygen; $C_1$–$C_{18}$alkyl which is substituted by hydroxy;

$R_6$ is hydrogen, $C_1$–$C_{18}$alkyl, $C_2$–$C_{18}$alkyl which is interrupted by oxygen; $C_2$–$C_{18}$alkyl which is substituted by hydroxy; or $C_7$–$C_{12}$phenylalkyl, which process comprises reacting a compound of the formula II:

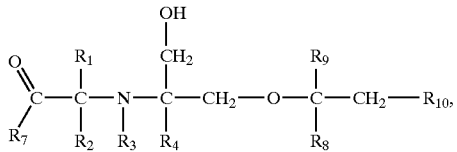

(II)

wherein $R_1$, $R_2$, $R_3$ and $R_4$ are as defined above, $R_7$ is hydroxy,

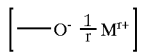

or $C_1$–$C_{18}$alkoxy, $R_8$ and $R_9$ are each independently of the other $C_1$–$C_{18}$alkyl, $C_2$–$C_{18}$alkyl which is interrupted by oxygen or by

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy;

$R_{10}$ is hydrogen, $C_1$–$C_{18}$alkyl, $C_2$–$C_{18}$alkyl which is interrupted by oxygen or by

$C_1$–$C_{18}$alkyl which is substituted by hydroxy; $C_7$–$C_{12}$phenylalkyl, $C_7$–$C_{12}$phenylalkyl substituted by hydroxy, $C_1$–$C_4$alkyl and/or $C_1$–$C_4$alkoxy; $C_5$–$C_{12}$cycloalkyl, $C_5$–$C_{12}$cycloalkyl substituted by hydroxy, $C_1$–$C_4$alkyl and/or $C_1$–$C_4$alkoxy;

M is a r-valent metal cation, and r is 1, 2 or 3, with a compound of the formula III:

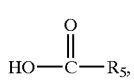

(III)

wherein $R_5$ is as defined above.

2. A process according to claim 1, $R_1$ and $R_2$ are each independently of the other $C_1$–$C_{12}$alkyl, $C_2$–$C_{12}$alkyl which is interrupted by oxygen or by

$C_1$–$C_{12}$alkyl which is substituted by hydroxy; $C_7$–$C_9$phenylalkyl, $C_7$–$C_9$phenylalkyl substituted by $C_1$–$C_4$alkyl and/or $C_1$–$C_4$alkoxy; $C_5$–$C_8$cycloalkyl, $C_5$–$C_8$cycloalkyl substituted by $C_1$–$C_4$alkyl and/or $C_1$–$C_4$alkoxy; or $R_1$ and $R_2$, together with the carbon atom to which they are bonded, form a $C_5$–$C_8$cycloalkylidene;

$R_3$ is hydrogen, $C_1$–$C_{12}$alkyl, $C_2$–$C_{12}$alkyl which is interrupted by oxygen or by

$C_1$–$C_{12}$alkyl which is substituted by hydroxy; $C_7$–$C_9$phenylalkyl, $C_7$–$C_9$phenylalkyl substituted by $C_1$–$C_4$alkyl and/or $C_1$–$C_4$alkoxy; $C_5$–$C_8$cycloalkyl, $C_5$–$C_8$cycloalkyl substituted by $C_1$–$C_4$alkyl and/or $C_1$–$C_4$alkoxy; $C_1$–$C_8$alkoxy, $C_5$–$C_8$cycloalkoxy, $C_2$–$C_8$alkenyloxy, $C_7$–$C_9$phenylalkoxy, $C_7$–$C_9$phenylalkoxy substituted by $C_1$–$C_4$alkyl and/or $C_1$–$C_4$alkoxy;

$R_4$ is $C_1$–$C_{12}$alkyl, $C_2$–$C_{12}$alkyl which is interrupted by oxygen or by

$C_1$–$C_{12}$alkyl which is substituted by hydroxy; $C_7$–$C_9$phenylalkyl, $C_7$–$C_9$phenylalkyl substituted $C_1$–$C_4$alkyl and/or $C_1$–$C_4$alkoxy; $C_5$–$C_8$cycloalkyl, $C_5$–$C_8$cycloalkyl substituted by $C_1$–$C_4$alkyl and/or $C_1$–$C_4$alkoxy;

$R_5$ is $C_1$–$C_{12}$alkyl, $C_2$–$C_{12}$alkyl which is interrupted by oxygen; $C_1$–$C_{12}$alkyl which is substituted by hydroxy;

$R_6$ is hydrogen, $C_1$–$C_{12}$alkyl, $C_2$–$C_{12}$alkyl which is interrupted by oxygen; $C_2$–$C_{12}$alkyl which is substituted by hydroxy; or $C_7$–$C_{12}$phenylalkyl, $R_7$ is hydroxy,

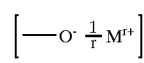

or $C_1$–$C_{12}$alkoxy, $R_8$ and $R_9$ are each independently of the other $C_1$–$C_{12}$alkyl, $C_2$–$C_{12}$alkyl which is interrupted by oxygen or by

$C_1$–$C_{12}$alkyl which is substituted by hydroxy; $C_7$–$C_9$phenylalkyl, $C_7$–$C_9$phenylalkyl substituted by $C_1$–$C_4$alkyl and/or $C_1$–$C_4$alkoxy; $C_5$–$C_8$cycloalkyl, $C_5$–$C_8$cycloalkyl substituted by $C_1$–$C_4$alkyl and/or $C_1$–$C_4$alkoxy;

R$_{10}$ is hydrogen, C$_1$–C$_{12}$alkyl, C$_2$–C$_{12}$alkyl which is interrupted by oxygen or by

C$_1$–C$_{12}$alkyl which is substituted by hydroxy; C$_7$–C$_9$phenylalkyl, C$_7$–C$_9$phenylalkyl substituted by C$_1$–C$_4$alkyl and/or C$_1$–C$_4$alkoxy; C$_5$–C$_8$cycloalkyl, C$_5$–C$_8$cycloalkyl substituted by C$_1$–C$_4$alkyl and/or C$_1$–C$_4$alkoxy;

M is a r-valent metal cation, and r is 1 or 2.

3. A process according to claim 1, wherein

R$_1$ and R$_2$ are each independently of the other C$_1$–C$_8$alkyl, C$_2$–C$_8$alkyl which is interrupted by oxygen; C$_1$–C$_8$alkyl which is substituted by hydroxy; benzyl, cyclohexyl; or R$_1$ and R$_2$, together with the carbon atom to which they are bonded, form a cyclohexylidene;

R$_3$ is hydrogen, C$_1$–C$_8$alkyl, C$_2$–C$_8$alkyl which is interrupted by oxygen; C$_1$–C$_8$alkyl which is substituted by hydroxy; benzyl, cyclohexyl, C$_1$–C$_8$alkoxy, cyclohexyloxy or benzyloxy;

R$_4$ is C$_1$–C$_8$alkyl, C$_2$–C$_8$alkyl which is interrupted by oxygen; C$_1$–C$_8$alkyl which is substituted by hydroxy; benzyl or cyclohexyl, R$_5$ is C$_1$–C$_{12}$alkyl or C$_1$–C$_{12}$alkyl which is substituted by hydroxy;

R$_7$ is hydroxy,

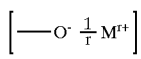

or C$_1$–C$_4$alkoxy,

R$_8$ and R$_9$ are each independently of the other C$_1$–C$_8$alkyl, C$_2$–C$_8$alkyl which is interrupted by oxygen; C$_1$–C$_8$alkyl which is substituted by hydroxy; benzyl or cyclohexyl, R$_{10}$ is hydrogen, C$_1$–C$_8$alkyl, C$_2$–C$_8$alkyl which is interrupted by oxygen; C$_1$–C$_8$alkyl which is substituted by hydroxy; benzyl or cyclohexyl, M is sodium, potassium, magnesium or calcium, and r is 1 or2.

4. A process according to claim 1, wherein

R$_1$ and R$_2$ are C$_1$–C$_4$alkyl,

R$_3$ is hydrogen or methyl.

R$_4$ is C$_1$–C$_4$alkyl,

R$_5$ is C$_1$–C$_{10}$alkyl,

R$_7$is hydroxy or

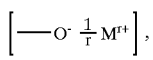

R$_8$ is C$_1$–C$_4$alkyl,

R$_9$ is C$_1$–C$_4$alkyl,

R$_{10}$ is hydrogen or C$_1$–C$_4$alkyl,

M is lithium, sodium, potassium or calcium, and r is 1 or 2.

5. A process according to claim 1, wherein

R$_1$ and R$_2$ are methyl,

R$_3$ is hydrogen,

R$_4$ is methyl or ethyl,

R$_5$ is C$_6$–C$_8$alkyl,

R$_7$ is

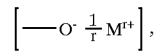

R$_8$ is methyl,

R$_9$ is methyl,

R$_{10}$ is hydrogen,

M is sodium, and r is 1.

6. A process according to claim 1, which process comprises reacting a compound of the formula II with a compound of the formula III in the presence of a catalyst.

7. A process according to claim 6, wherein the catalyst is a Brönstedt acid or a Lewis acid.

8. A compound of the formula II:

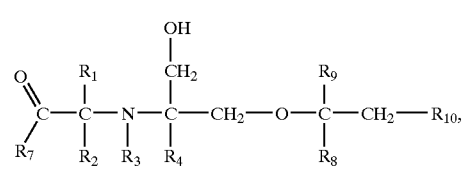

(II)

wherein

R$_1$ and R$_2$ are each independently of the other C$_1$–C$_{18}$alkyl, C$_2$–C$_{18}$alkyl which is interrupted by oxygen or by

C$_1$–C$_{18}$alkyl which is substituted by hydroxy; C$_7$–C$_{12}$phenylalkyl, C$_7$–C$_{12}$phenylalkyl substituted by hydroxy, C$_1$–C$_4$alkyl and/or C$_1$–C$_4$alkoxy; C$_5$–C$_{12}$cycloalkyl, C$_5$–C$_{12}$cycloalkyl substituted by hydroxy, C$_1$–C$_4$alkyl and/or C$_1$–C$_4$alkoxy; or R$_1$ and R$_2$, together with the carbon atom to which they are bonded, form a C$_5$–C$_8$cycloalkylidene ring unsubstituted or substituted by from 1 to 3 C$_1$–C$_4$alkyl groups;

R$_3$ is hydrogen, C$_1$–C$_{18}$alkyl, C$_2$–C$_{18}$alkyl which is interrupted by oxygen or by

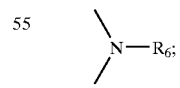

C$_1$–C$_{18}$alkyl which is substituted by hydroxy; C$_7$–C$_{12}$phenylalkyl, C$_7$–C$_{12}$phenylalkyl substituted by hydroxy, C$_1$–C$_4$alkyl and/or C$_1$–C$_4$alkoxy; C$_5$–C$_{12}$cycloalkyl, C$_5$–C$_{12}$cycloalkyl substituted by hydroxy, C$_1$–C$_4$alkyl and/or C$_1$–C$_4$alkoxy; C$_1$–C$_{12}$alkoxy, C$_5$–C$_{12}$cycloalkoxy, C$_2$–C$_{12}$alkenyloxy, C$_7$–C$_{12}$phenylalkoxy, C$_7$–C$_{12}$phenylalkoxy substituted by hydroxy, C$_1$–C$_4$alkyl and/or C$_1$–C$_4$alkoxy;

R$_4$ is C$_1$–C$_{18}$alkyl, C$_2$–C$_{18}$alkyl which is interrupted by oxygen or by

C$_1$–C$_{18}$alkyl which is substituted by hydroxy; C$_7$–C$_{12}$phenylalkyl, C$_7$–C$_{12}$phenylalkyl substituted by hydroxy, C$_1$–C$_4$alkyl and/or C$_1$–C$_4$alkoxy; C$_5$–C$_{12}$cycloalkyl, C$_5$–C$_{12}$cycloalkyl substituted by hydroxy, C$_1$–C$_4$alkyl and/or C$_1$–C$_4$alkoxy;

R$_6$ is hydrogen, C$_1$–C$_{18}$alkyl, C$_2$–C$_{18}$alkyl which is interrupted by oxygen; C$_2$–C$_{18}$alkyl which is substituted by hydroxy; or C$_7$–C$_{12}$phenylalkyl, R$_7$ is hydroxy,

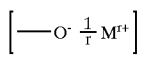

or C$_1$–C$_{18}$alkoxy,

R$_8$ and R$_9$ are each independently of the other C$_1$–C$_{18}$alkyl, C$_2$–C$_{18}$alkyl which is interrupted by oxygen or by

C$_1$–C$_{18}$alkyl which is substituted by hydroxy; C$_7$–C$_{12}$phenylalkyl, C$_7$–C$_{12}$phenylalkyl substituted by hydroxy, C$_1$–C$_4$alkyl and/or C$_1$–C$_4$alkoxy; C$_5$–C$_{12}$cycloalkyl, C$_5$–C$_{12}$cycloalkyl substituted by hydroxy, C$_1$–C$_4$alkyl and/or C$_1$–C$_4$alkoxy;

R$_{10}$ is hydrogen, C$_1$–C$_{18}$alkyl, C$_2$–C$_{18}$alkyl which is interrupted by oxygen or by

C$_1$–C$_{18}$alkyl which is substituted by hydroxy; C$_7$–C$_{12}$phenylalkyl, C$_7$–C$_{12}$phenylalkyl substituted by hydroxy, C$_1$–C$_4$alkyl and/or C$_1$–C$_4$alkoxy; C$_5$–C$_{12}$cycloalkyl, C$_5$–C$_{12}$cycloalkyl substituted by hydroxy, C$_1$–C$_4$alkyl and/or C$_1$–C$_4$alkoxy;

M is a r-valent metal cation, and r is 1, 2 or 3.

9. A compound according to claim 8, wherein

R$_1$ and R$_2$ are C$_1$–C$_4$alkyl,

R$_3$ is hydrogen or methyl,

R$_4$ is C$_1$–C$_4$alkyl,

R$_7$ is hydroxy or

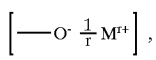,

R$_8$ is C$_1$–C$_4$alkyl,

R$_9$ is C$_1$–C$_4$alkyl,

R$_{10}$ is hydrogen or C$_1$–C$_4$alkyl,

M is lithium, sodium, potassium or calcium, and r is 1 or 2.

10. A process for the preparation of compounds of the formula II:

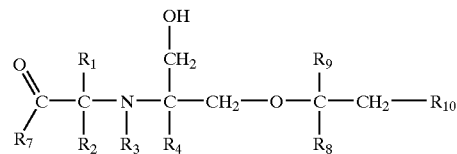

(II)

wherein

R$_1$ and R$_2$ are each independently of the other C$_1$–C$_{18}$alkyl, C$_2$–C$_{18}$alkyl which is interrupted by oxygen or by

C$_1$–C$_{18}$alkyl which is substituted by hydroxy; C$_7$–C$_{12}$phenylalkyl, C$_7$–C$_{12}$phenylalkyl substituted by hydroxy, C$_1$–C$_4$alkyl and/or C$_1$–C$_4$alkoxy; C$_5$–C$_{12}$cycloalkyl, C$_5$–C$_{12}$cycloalkyl substituted by hydroxy, C$_1$–C$_4$alkyl and/or C$_1$–C$_4$alkoxy; or R$_1$ and R$_2$, together with the carbon atom to which they are bonded, form a C$_5$–C$_8$cycloalkylidene ring unsubstituted or substituted by from 1 to 3 C$_1$–C$_4$alkyl groups;

R$_3$ is hydrogen, C$_1$–C$_{18}$alkyl, C$_2$–C$_{18}$alkyl which is interrupted by oxygen or by

C$_1$–C$_{18}$alkyl which is substituted by hydroxy; C$_7$–C$_{12}$phenylalkyl, C$_7$–C$_{12}$phenylalkyl substituted by hydroxy, C$_1$–C$_4$alkyl and/or C$_1$–C$_4$alkoxy; C$_5$–C$_{12}$cycloalkyl, C$_5$–C$_{12}$cycloalkyl substituted by hydroxy, C$_1$–C$_4$alkyl and/or C$_1$–C$_4$alkoxy; C$_1$–C$_{12}$alkoxy, C$_5$–C$_{12}$cycloalkoxy, C$_2$–C$_{12}$alkenyloxy, C$_7$–C$_{12}$phenylalkoxy, C$_7$–C$_{12}$phenylalkoxy substituted by hydroxy, C$_1$–C$_4$alkyl and/or C$_1$–C$_4$alkoxy;

R$_4$ is C$_1$–C$_{18}$alkyl, C$_2$–C$_{18}$alkyl which is interrupted by oxygen or by

C$_1$–C$_{18}$alkyl which is substituted by hydroxy; C$_7$–C$_{12}$phenylalkyl, C$_7$–C$_{12}$phenylalkyl substituted by hydroxy, C$_1$–C$_4$alkyl and/or C$_1$–C$_4$alkoxy; C$_5$–C$_{12}$cycloalkyl, C$_5$–C$_{12}$cycloalkyl substituted by hydroxy, C$_1$–C$_4$alkyl and/or C$_1$–C$_4$alkoxy;

R$_6$ is hydrogen, C$_1$–C$_{18}$alkyl, C$_2$–C$_{18}$alkyl which is interrupted by oxygen; C$_2$–C$_{18}$alkyl which is substituted by hydroxy; or C$_7$–C$_{12}$phenylalkyl, R$_7$ is hydroxy,

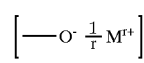

or C$_1$–C$_{18}$alkoxy,

R$_8$ and R$_9$ are each independently of the other C$_1$–C$_{18}$alkyl, C$_2$–C$_{18}$alkyl which is interrupted by oxygen or by

C$_1$–C$_{18}$alkyl which is substituted by hydroxy; C$_7$–C$_{12}$phenylalkyl, C$_7$–C$_{12}$phenylalkyl substituted by hydroxy, C$_1$–C$_4$alkyl and/or C$_1$–C$_4$alkoxy; C$_5$–C$_{12}$cycloalkyl, C$_5$–C$_{12}$cycloalkyl substituted by hydroxy, C$_1$–C$_4$alkyl and/or C$_1$–C$_4$alkoxy;

R$_{10}$ is hydrogen, C$_1$–C$_{18}$alkyl, C$_2$–C$_{18}$alkyl which is interrupted by oxygen or by

C$_1$–C$_{18}$alkyl which is substituted by hydroxy; C$_7$–C$_{12}$phenylalkyl, C$_7$–C$_{12}$phenylalkyl substituted by hydroxy, C$_1$–C$_4$alkyl and/or C$_1$–C$_4$alkoxy; C$_5$–C$_{12}$cycloalkyl, C$_5$–C$_{12}$cycloalkyl substituted by hydroxy, C$_1$–C$_4$alkyl and/or C$_1$–C$_4$alkoxy;

M is a r-valent metal cation, and
r is 1, 2 or 3;

which process comprises reacting a compound of the formula IV:

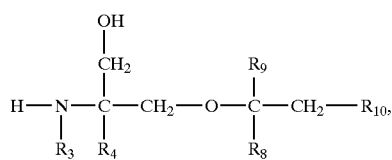

(IV)

wherein R$_3$, R$_4$, R$_8$, R$_9$ and R$_{10}$ are as defined above, with a compound of the formula V:

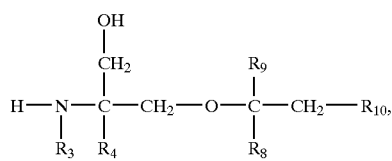

(V)

wherein R$_1$ and R$_2$ are as defined above, and chloroform in the presence of a base.

11. A compound of the formula IV:

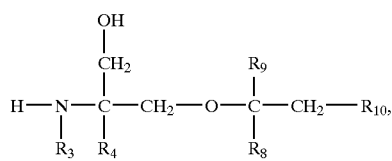

(IV)

wherein
R$_3$ is hydrogen, C$_1$–C$_{18}$alkyl, C$_2$–C$_{18}$alkyl which is interrupted by oxygen or by

C$_1$–C$_{18}$alkyl which is substituted by hydroxy; C$_7$–C$_{12}$phenylalkyl, C$_7$–C$_{12}$phenylalkyl substituted by hydroxy, C$_1$–C$_4$alkyl and/or C$_1$–C$_4$alkoxy; C$_5$–C$_{12}$cycloalkyl, C$_5$–C$_{12}$cycloalkyl substituted by hydroxy, C$_1$–C$_4$alkyl and/or C$_1$–C$_4$alkoxy; C$_1$–C$_{12}$alkoxy, C$_5$–C$_{12}$cycloalkoxy, C$_2$–C$_{12}$alkenyloxy, C$_7$–C$_{12}$phenylalkoxy, C$_7$–C$_{12}$phenylalkoxy substituted by hydroxy, C$_1$–C$_4$alkyl and/or C$_1$–C$_4$alkoxy;

R$_4$ is C$_1$–C$_{18}$alkyl, C$_2$–C$_{18}$alkyl which is interrupted by oxygen or by

C$_1$–C$_{18}$alkyl which is substituted by hydroxy; C$_7$–C$_{12}$phenylalkyl, C$_7$–C$_{12}$phenylalkyl substituted by hydroxy, C$_1$–C$_4$alkyl and/or C$_1$–C$_4$alkoxy; C$_5$–C$_{12}$cycloalkyl, C$_5$–C$_{12}$cycloalkyl substituted by hydroxy, C$_1$–C$_4$alkyl and/or C$_1$–C$_4$alkoxy;

R$_6$ is hydrogen, C$_1$–C$_{18}$alkyl, C$_2$–C$_{18}$alkyl which is interrupted by oxygen; C$_2$–C$_{18}$alkyl which is substituted by hydroxy; or C$_7$–C$_{12}$phenylalkyl, R$_8$ and R$_9$ are each independently of the other C$_1$–C$_{18}$alkyl, C$_2$–C$_{18}$alkyl which is interrupted by oxygen or by

C$_1$–C$_{18}$alkyl which is substituted by hydroxy; C$_7$–C$_{12}$phenylalkyl, C$_7$–C$_{12}$phenylalkyl substituted by hydroxy, C$_1$–C$_4$alkyl and/or C$_1$–C$_4$alkoxy; C$_5$–C$_{12}$cycloalkyl, C$_5$–C$_{12}$cycloalkyl substituted by hydroxy, C$_1$–C$_4$alkyl and/or C$_1$–C$_4$alkoxy;

R$_{10}$ is hydrogen, C$_1$–C$_{18}$alkyl, C$_2$–C$_{18}$alkyl which is interrupted by oxygen or by

C$_1$–C$_{18}$alkyl which is substituted by hydroxy; C$_7$–C$_{12}$phenylalkyl, C$_7$–C$_{12}$phenylalkyl substituted by hydroxy, C$_1$–C$_4$alkyl and/or C$_1$–C$_4$alkoxy; C$_5$–C$_{12}$cycloalkyl, C$_5$–C$_{12}$cydoalkyl substituted by hydroxy, C$_1$–C$_4$alkyl and/or C$_1$–C$_4$alkoxy.

12. A compound according to claim 11, wherein
R$_3$ is hydrogen or methyl,
R$_4$ is C$_1$–C$_4$alkyl,
R$_8$ and R$_9$ is C$_1$–C$_4$alkyl, and
R$_{10}$ is hydrogen or C$_1$–C$_4$alkyl.

13. A process for the preparation of compounds of the formula I:

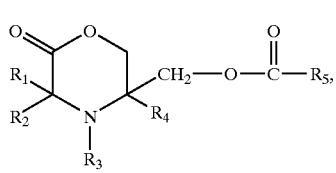

(I)

wherein the variables R$_1$–R$_5$ are as defined in claim 1, which comprises in successive steps a) reacting a compound of the formula VI:

$$R_4\text{—}CH_2\text{—}NO_2 \quad \text{(VI)},$$

wherein $R_4$ is as defined in claim 1, with formaldehyde in the presence of a base to give the compound of the formula VII:

$$O_2N\text{—}\underset{R_4}{CH}\text{—}CH_2\text{—}OH, \quad \text{(VII)}$$

and then b) reacting this compound of the formula VII with a compound of the formula VIII or IX:

$$\underset{R_4}{\overset{R_9}{C}}{=}CH\text{—}R_{10} \quad \text{(VIII)}$$

$$HO\text{—}\underset{R_8}{\overset{R_9}{C}}\text{—}CH_2\text{—}R_{10} \quad \text{(IX)}$$

wherein $R_8$, $R_9$ and $R_{10}$ are as defined in claim 1, in the presence of a catalyst to give the compound of the formula X:

$$O_2N\text{—}\underset{R_4}{CH}\text{—}CH_2\text{—}O\text{—}\underset{R_8}{\overset{R_9}{C}}\text{—}CH_2\text{—}R_{10} \quad \text{(X)}$$

and then c) reacting this compound of the formula X with formaldehyde in the presence of a base to give the compound of the formula XI:

$$O_2N\text{—}\underset{R_4}{\overset{\overset{\overset{OH}{|}}{CH_2}}{CH}}\text{—}CH_2\text{—}O\text{—}\underset{R_8}{\overset{R_9}{C}}\text{—}CH_2\text{—}R_{10} \quad \text{(XI)}$$

and then d) reacting this compound of the formula XI with hydrogen in the presence of a catalyst to give the compound of the formula IV:

$$H\text{—}\underset{R_3}{N}\text{—}\underset{R_4}{\overset{\overset{\overset{OH}{|}}{CH_2}}{C}}\text{—}CH_2\text{—}O\text{—}\underset{R_8}{\overset{R_9}{C}}\text{—}CH_2\text{—}R_{10} \quad \text{(IV)}$$

wherein $R_3$ is hydrogen, and then e) for obtaining the compounds of the formula IV wherein $R_3$ is different from hydrogen, reacting the compound of the formula IV with an alkylation reagent; and then f) reacting the compound of the formula IV with a compound of the formula V:

$$R_1\overset{\overset{O}{\|}}{C}R_2, \quad \text{(V)}$$

wherein $R_1$ and $R_2$ are as defined in claim 1, and chloroform in the presence of a base to give the compound of the formula II:

$$\underset{R_7}{\overset{O}{\|}}C\text{—}\underset{R_2}{\overset{R_1}{C}}\text{—}\underset{R_3}{N}\text{—}\underset{R_4}{\overset{\overset{\overset{OH}{|}}{CH_2}}{C}}\text{—}CH_2\text{—}O\text{—}\underset{R_8}{\overset{R_9}{C}}\text{—}CH_2\text{—}R_{10}, \quad \text{(II)}$$

wherein $R_7$ is as defined in claim 1, and then g) for obtaining a compound of the formula II wherein $R_3$ is different from hydrogen, reacting the compound of the formula II, wherein $R_3$ is hydrogen, with an alkylation reagent in case of step e) being not present; and then h) reacting this compound of the formula II with a compound of the formula III:

$$HO\text{—}\overset{\overset{O}{\|}}{C}\text{—}R_5, \quad \text{(III)}$$

wherein $R_5$ is as defined in claim 1; and then i) for obtaining a compound of the formula I wherein $R_3$ is different from hydrogen, reacting the compound of the formula I, wherein $R_3$ is hydrogen, with an alkylation reagent in case of steps e) and g) being not present.

14. A process for the preparation of compounds of the formula I:

(I)

wherein the variables $R_1$–$R_5$ are as defined in claim 1, which comprises in successive steps a) reacting a compound of the formula VI:

$$R_4\text{—}CH_2\text{—}NO_2 \quad \text{(VI)},$$

wherein $R_4$ is as defined in claim 1, with formaldehyde in the presence of a base to give the compound of the formula XII:

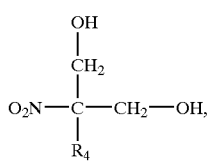
(XII)

and then
  b) reacting this compound of the formula XII with a compound of the formula VIII or IX

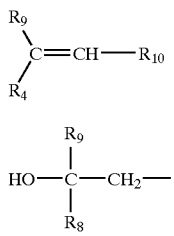
(VIII)

(IX)

wherein $R_8$, $R_9$ and $R_{10}$ are as defined in claim 1, in the presence of a catalyst to give the compound of the formula XI:

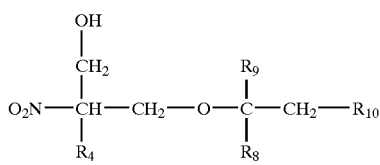
(XI)

and then
  c) reacting this compound of the formula XI with hydrogen in the presence of a catalyst to give the compound of the formula IV:

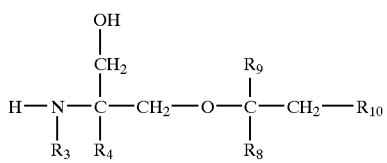
(IV)

wherein $R_3$ is hydrogen, and then
  d) for obtaining the compounds of the formula IV wherein $R_3$ is different from hydrogen, reacting the compound of the formula IV with an alkylation reagent; and then
  e) reacting the compound of the formula IV with a compound of the formula V:

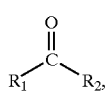
(V)

wherein $R_1$ and $R_2$ are as defined in claim 1, and chloroform in the presence of a base to give the compound of the formula II:

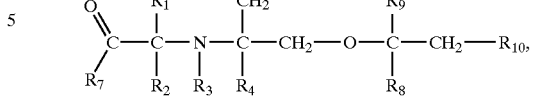
(II)

wherein $R_7$ is as defined in claim 1, and then
  f) for obtaining a compound of the formula II wherein $R_3$ is different from hydrogen, reacting the compound of the formula II, wherein $R_3$ is hydrogen, with an alkylation reagent in case of step d) being not present; and then
  g) reacting this compound of the formula II with a compound of the formula III:

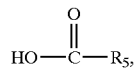
(III)

wherein $R_5$ is as defined in claim 1; and then
  h) for obtaining a compound of the formula I wherein $R_3$ is different from hydrogen, reacting the compound of the formula I, wherein $R_3$ is hydrogen, with an alkylation reagent in case of steps d) and f) being not present.

15. A composition comprising:
  a) an organic material which is susceptible to oxidative, thermal or light-induced degradation, and
  b) at least one compound of the formula II according to claim 8.

16. A composition according to claim 15, comprising as component (a) a synthetic polymer, a reprographic material or a coating material.

17. A composition according to claim 15, wherein component (b) is present in an amount of from 0.1 to 10%, based on the weight of component (a).

18. A composition according to claim 15, comprising in addition, besides components (a) and (b), further additives selected from the group consisting of colorants, antioxidants, peroxide scavengers, thiosynergists, basic co-stabilizers, further light stabilizers, metal passivators, viscosity imorovers, brighteners, biocides, antistats, solvents, plasticizers, thixotronic agents, levelling assistants, lubricants, emulsifiers, catalysts, flow-control agents, flame-proofing agents, blowing agents, fillers, reinforcing agents and nucleating agents.

19. A composition according to claim 18, comprising as further additives phenolic antioxidants, light-stabilizers, processing stabilizers, solvents, pigments, dyes, plasticizers, thixotropic agents, levelling assistants, further light stabilizers and/or metal passivators.

20. A composition according to claim 18, comprising as further additives a stabilizer selected from the class of the 2-hydroxyphenyl-triazines and/or 2-hydroxyphenyl-benzotriazoles.

21. A process for stabilizing an organic material against oxidative, thermal or light-induced degradation, which comprises incorporating therein or applying thereto at least one compound of the formula II according to claim 8.

* * * * *